US008467876B2

(12) United States Patent
Tehrani

(10) Patent No.: US 8,467,876 B2
(45) Date of Patent: Jun. 18, 2013

(54) BREATHING DISORDER DETECTION AND THERAPY DELIVERY DEVICE AND METHOD

(75) Inventor: Amir J. Tehrani, San Francisco, CA (US)

(73) Assignee: RMX, LLC, San Francisco, CA (US)

( * ) Notice: Subject to any disclaimer, the term of this patent is extended or adjusted under 35 U.S.C. 154(b) by 1081 days.

(21) Appl. No.: 10/686,891

(22) Filed: Oct. 15, 2003

(65) Prior Publication Data

US 2005/0085865 A1 Apr. 21, 2005

(51) Int. Cl.
*A61N 1/18* (2006.01)
(52) U.S. Cl.
USPC ............................................ 607/42
(58) Field of Classification Search
USPC ............................. 607/42, 20, 116; 600/534
See application file for complete search history.

(56) References Cited

U.S. PATENT DOCUMENTS

| 3,773,051 | A | | 11/1973 | Holcomb et al. | |
| 4,827,935 | A | * | 5/1989 | Geddes et al. | 607/42 |
| 4,830,008 | A | * | 5/1989 | Meer | 607/42 |
| 5,056,519 | A | | 10/1991 | Vince | 128/419 |
| 5,146,918 | A | * | 9/1992 | Kallok et al. | 607/2 |
| 5,174,287 | A | | 12/1992 | Kallok et al. | 128/419 |
| 5,190,036 | A | | 3/1993 | Linder | |
| 5,211,173 | A | | 5/1993 | Kallok et al. | 128/419 |
| 5,215,082 | A | | 6/1993 | Kallok et al. | 128/419 |
| 5,233,983 | A | | 8/1993 | Markowitz | 607/42 |
| 5,265,604 | A | | 11/1993 | Vince | 607/42 |
| 5,281,219 | A | | 1/1994 | Kallok | 607/42 |
| 5,300,094 | A | | 4/1994 | Kallok et al. | 607/42 |
| 5,423,327 | A | * | 6/1995 | Clauson et al. | 600/322 |
| 5,483,969 | A | | 1/1996 | Testerman et al. | |
| 5,485,851 | A | | 1/1996 | Erickson | 128/716 |
| 5,522,862 | A | * | 6/1996 | Testerman et al. | 607/42 |
| 5,524,632 | A | | 6/1996 | Stein et al. | 128/733 |
| 5,540,731 | A | | 7/1996 | Testerman | 607/42 |
| 5,540,732 | A | | 7/1996 | Testerman et al. | 607/42 |
| 5,540,733 | A | | 7/1996 | Testerman et al. | 607/42 |
| 5,546,952 | A | | 8/1996 | Erickson | |
| 5,549,655 | A | | 8/1996 | Erickson | |
| 5,572,543 | A | | 11/1996 | Heinemann et al. | |
| 5,678,535 | A | | 10/1997 | DiMarco | 128/200.24 |

(Continued)

FOREIGN PATENT DOCUMENTS

| DE | 112004001957 T5 | 8/2006 |
| DE | 112004001953 T5 | 10/2006 |

(Continued)

OTHER PUBLICATIONS

Shier, D., Butler, J. and Lewis, R., Hole's Human Anatomy and Physiology (Ninth Edition), McGraw-Hill 2002, p. 798.*

(Continued)

*Primary Examiner* — Niketa Patel
*Assistant Examiner* — Alyssa M Alter
(74) *Attorney, Agent, or Firm* — Levine Bagade Han LLP

(57) ABSTRACT

A device and method are provided for managing the treatment of a patient with respiratory disorders or symptoms. Respiratory parameters are sensed and recorded and communicated to an external device to provide information to a patient and/or provider for further treatment or diagnosis. Also respiratory disorders such as apnea or hypoventilation may be treated by electrically stimulating the diaphragm muscle or phrenic nerve in response to a sensed respiratory parameter or characteristic.

8 Claims, 13 Drawing Sheets

U.S. PATENT DOCUMENTS

| | | | | |
|---|---|---|---|---|
| 5,766,228 A * | 6/1998 | Bonnet et al. | | 607/16 |
| 5,797,923 A | 8/1998 | Aiyar et al. | | 606/129 |
| 5,800,470 A | 9/1998 | Stein et al. | | 607/20 |
| 5,814,086 A | 9/1998 | Hirschberg | | |
| 5,830,008 A | 11/1998 | Broschard, III | | |
| 5,876,353 A | 3/1999 | Riff | | 600/547 |
| 5,895,360 A * | 4/1999 | Christopherson et al. | | 607/42 |
| 5,911,218 A | 6/1999 | DiMarco | | 128/200.24 |
| 5,944,680 A | 8/1999 | Christopherson | | |
| 6,021,352 A | 2/2000 | Christopherson et al. | | 607/42 |
| 6,099,479 A | 8/2000 | Christopherson et al. | | 600/529 |
| 6,212,435 B1 | 4/2001 | Lattner et al. | | 607/134 |
| 6,224,562 B1 | 5/2001 | Lurie et al. | | 601/41 |
| 6,251,126 B1 * | 6/2001 | Ottenhoff et al. | | 607/42 |
| 6,269,269 B1 | 7/2001 | Ottenhoff et al. | | 607/42 |
| 6,312,399 B1 | 11/2001 | Lurie et al. | | |
| 6,314,324 B1 | 11/2001 | Lattner et al. | | |
| 6,345,202 B2 | 2/2002 | Richmond et al. | | 607/42 |
| 6,415,183 B1 * | 7/2002 | Scheiner et al. | | 607/42 |
| 6,463,327 B1 | 10/2002 | Lurie | | |
| 6,480,733 B1 | 11/2002 | Turcott | | 600/516 |
| 6,512,949 B1 | 1/2003 | Combs et al. | | |
| 6,527,729 B1 | 3/2003 | Turcott | | 600/528 |
| 6,542,774 B2 | 4/2003 | Hill | | |
| 6,572,543 B1 | 6/2003 | Christopherson et al. | | 600/300 |
| 6,574,507 B1 | 6/2003 | Bonnet | | 607/20 |
| 6,587,725 B1 | 7/2003 | Durand et al. | | |
| 6,587,726 B2 | 7/2003 | Lurie et al. | | |
| 6,589,188 B1 | 7/2003 | Street et al. | | 600/538 |
| 6,600,949 B1 | 7/2003 | Turcott | | 600/518 |
| 6,633,779 B1 | 10/2003 | Schuler et al. | | |
| 6,731,984 B2 | 5/2004 | Cho et al. | | 607/17 |
| 6,735,479 B2 | 5/2004 | Fabian et al. | | |
| 6,752,765 B1 | 6/2004 | Jensen et al. | | 600/536 |
| 6,770,022 B2 | 8/2004 | Mechlenburg et al. | | |
| 6,811,537 B2 | 11/2004 | Bardy | | |
| 6,830,548 B2 | 12/2004 | Bonnet et al. | | 600/529 |
| 6,881,192 B1 | 4/2005 | Park et al. | | |
| 6,908,437 B2 | 6/2005 | Bardy | | |
| 7,058,453 B2 | 6/2006 | Nelson et al. | | |
| 7,070,568 B1 | 7/2006 | Koh et al. | | |
| 7,082,331 B1 | 7/2006 | Park et al. | | |
| 7,117,032 B2 | 10/2006 | Childre et al. | | |
| 7,277,757 B2 | 10/2007 | Casavant et al. | | |
| 7,532,934 B2 | 5/2009 | Lee et al. | | |
| 7,610,094 B2 | 10/2009 | Stahmann et al. | | |
| 7,840,270 B2 | 11/2010 | Ignagni et al. | | |
| 7,970,475 B2 | 6/2011 | Tehrani et al. | | |
| 7,979,128 B2 | 7/2011 | Tehrani et al. | | |
| 8,116,872 B2 | 2/2012 | Tehrani et al. | | |
| 8,140,164 B2 | 3/2012 | Tehrani et al. | | |
| 8,255,056 B2 | 8/2012 | Tehrani | | |
| 8,280,513 B2 | 10/2012 | Tehrani et al. | | |
| 2002/0049482 A1 | 4/2002 | Fabian et al. | | |
| 2002/0193697 A1 | 12/2002 | Cho et al. | | 600/529 |
| 2002/0193839 A1 | 12/2002 | Cho et al. | | 607/17 |
| 2003/0127091 A1 | 7/2003 | Chang | | |
| 2003/0153953 A1 | 8/2003 | Park et al. | | 607/17 |
| 2003/0153954 A1 * | 8/2003 | Park et al. | | 607/17 |
| 2003/0153955 A1 | 8/2003 | Park et al. | | 607/17 |
| 2003/0153956 A1 | 8/2003 | Park et al. | | 607/17 |
| 2003/0195571 A1 | 10/2003 | Burnes et al. | | 607/9 |
| 2003/0204213 A1 | 10/2003 | Jensen et al. | | |
| 2003/0225339 A1 | 12/2003 | Orr et al. | | |
| 2004/0044377 A1 | 3/2004 | Larsson | | |
| 2004/0059240 A1 | 3/2004 | Cho et al. | | |
| 2004/0077953 A1 | 4/2004 | Turcott | | |
| 2004/0088015 A1 | 5/2004 | Casavant et al. | | 607/14 |
| 2004/0111040 A1 | 6/2004 | Ni et al. | | 600/534 |
| 2004/0116784 A1 | 6/2004 | Gavish | | |
| 2004/0122484 A1 | 6/2004 | Hatlestad et al. | | |
| 2004/0134496 A1 | 7/2004 | Cho et al. | | 128/204.23 |
| 2004/0138719 A1 | 7/2004 | Cho et al. | | 607/42 |
| 2004/0176809 A1 | 9/2004 | Cho et al. | | 607/14 |
| 2004/0199221 A1 | 10/2004 | Fabian et al. | | |
| 2004/0225226 A1 | 11/2004 | Lehrman et al. | | 600/529 |
| 2004/0237963 A1 | 12/2004 | Berthon-Jones | | 128/204.26 |
| 2005/0021102 A1 * | 1/2005 | Ignagni et al. | | 607/42 |
| 2005/0039745 A1 | 2/2005 | Stahmann et al. | | |
| 2005/0043644 A1 | 2/2005 | Stahmann et al. | | 600/529 |
| 2005/0043772 A1 | 2/2005 | Stahmann et al. | | 607/42 |
| 2005/0055060 A1 | 3/2005 | Koh et al. | | 607/17 |
| 2005/0061315 A1 | 3/2005 | Lee et al. | | 128/204.21 |
| 2005/0061319 A1 | 3/2005 | Hartley et al. | | 128/204.18 |
| 2005/0061320 A1 | 3/2005 | Lee et al. | | 128/204.18 |
| 2005/0065563 A1 | 3/2005 | Scheiner | | 607/9 |
| 2005/0065567 A1 | 3/2005 | Lee et al. | | 607/17 |
| 2005/0074741 A1 | 4/2005 | Lee et al. | | 434/433 |
| 2005/0076909 A1 | 4/2005 | Stahmann et al. | | |
| 2005/0080461 A1 | 4/2005 | Stahmann et al. | | 607/17 |
| 2005/0085734 A1 * | 4/2005 | Tehrani | | 600/484 |
| 2005/0085866 A1 * | 4/2005 | Tehrani | | 607/42 |
| 2005/0085867 A1 * | 4/2005 | Tehrani et al. | | 607/42 |
| 2005/0085868 A1 * | 4/2005 | Tehrani et al. | | 607/42 |
| 2005/0085869 A1 * | 4/2005 | Tehrani et al. | | 607/42 |
| 2005/0101833 A1 | 5/2005 | Hsu et al. | | 600/26 |
| 2005/0107860 A1 | 5/2005 | Ignagni et al. | | |
| 2005/0115561 A1 | 6/2005 | Stahmann et al. | | 128/200.24 |
| 2005/0119711 A1 | 6/2005 | Cho et al. | | |
| 2005/0145246 A1 | 7/2005 | Hartley et al. | | 128/203.14 |
| 2005/0148897 A1 | 7/2005 | Cho et al. | | 600/533 |
| 2005/0165457 A1 | 7/2005 | Benser et al. | | |
| 2005/0224076 A1 | 10/2005 | Pflchner et al. | | |
| 2005/0240240 A1 | 10/2005 | Park et al. | | |
| 2005/0261600 A1 | 11/2005 | Aylsworth | | |
| 2005/0261747 A1 | 11/2005 | Schuler et al. | | |
| 2006/0030894 A1 | 2/2006 | Tehrani | | |
| 2006/0036294 A1 | 2/2006 | Tehrani | | |
| 2006/0058852 A1 | 3/2006 | Koh et al. | | |
| 2006/0064030 A1 | 3/2006 | Cosentino et al. | | |
| 2006/0064325 A1 | 3/2006 | Matsumoto et al. | | |
| 2006/0122661 A1 | 6/2006 | Mandell | | |
| 2006/0122662 A1 | 6/2006 | Tehrani | | |
| 2006/0142815 A1 | 6/2006 | Tehrani et al. | | |
| 2006/0149334 A1 | 7/2006 | Tehrani et al. | | |
| 2006/0155341 A1 | 7/2006 | Tehrani et al. | | |
| 2006/0167523 A1 | 7/2006 | Tehrani et al. | | |
| 2006/0224211 A1 | 10/2006 | Durand et al. | | |
| 2006/0247729 A1 | 11/2006 | Tehrani et al. | | |
| 2006/0282131 A1 | 12/2006 | Caparso et al. | | |
| 2007/0021795 A1 | 1/2007 | Tehrani | | |
| 2007/0156199 A1 | 7/2007 | Koh et al. | | |
| 2008/0021506 A1 | 1/2008 | Grocela | | |
| 2008/0167695 A1 | 7/2008 | Tehrani et al. | | |
| 2008/0177347 A1 | 7/2008 | Tehrani et al. | | |
| 2008/0183239 A1 | 7/2008 | Tehrani et al. | | |
| 2008/0183240 A1 | 7/2008 | Tehrani et al. | | |
| 2008/0188903 A1 | 8/2008 | Tehrani et al. | | |
| 2008/0188904 A1 | 8/2008 | Tehrani et al. | | |
| 2008/0208281 A1 | 8/2008 | Tehrani et al. | | |
| 2011/0230932 A1 | 9/2011 | Tehrani et al. | | |
| 2012/0158091 A1 | 6/2012 | Tehrani et al. | | |

FOREIGN PATENT DOCUMENTS

| | | |
|---|---|---|
| DE | 112004001954 T5 | 10/2006 |
| WO | WO/8600234 | 1/1986 |
| WO | WO 2005/037077 | 4/2005 |
| WO | WO 2005/037172 | 4/2005 |
| WO | WO 2005/037173 | 4/2005 |
| WO | WO 2005/037174 | 4/2005 |
| WO | WO 2005/037220 | 4/2005 |
| WO | WO 2005/037366 | 4/2005 |
| WO | WO 2007/058938 | 5/2007 |

OTHER PUBLICATIONS

Don D. Sin, Effects of Continuous Positive Airway Pressure on Cardiovascular Outcomes in Heart Failure Patients With and Without Cheyne-Stokes Respiration, *Circulation*, 102:61-66 (Jul. 4, 2000).

Takaomi Taira, M.D., Ph.D., et. al, Phrenic Nerve Stimulation for Diaphragm Pacing With a Spinal Cord Stimulator, *Surg Neurol*, 59:128-132 (2003).

Donald B. Shaul, et. al, Thoracoscopic Placement of Phrenic Nerve Electrodes for Diaphragmatic Pacing in Children, *Journal of Pediatric Surgery*, 37:974-978 (Jul. 2002).

Christopher Reeve, New Implantable Breathing Device, *University Hospitals of Cleveland*, pp. 1-4, (2003).

Christopher Reeve, Christopher Reeve Paralysis Foundation Questions & Answers, pp. 1-3 (Mar. 13, 2003).
T. Mitsuyana, et. al, Diaphragm Pacing With the Spinal Cord Stimulator, *Aeta Neurochir*, 87:89-92 (2003).
Harish Aiyar, et. al, Laparoscopic Implant Device for Intermuscular Electrodes, IEEE-EMBC and CMBCC, pp. 1167-1168, ((1995).
Harish Aiyar,et.al. Laparoscopic Implant Instrument for the Placement of Intramuscular Electrodes in the Diaphragm, *Transactions on Rehabilitation Engineering*, pp. 360-371 (Sep. 1999).
Anthony F. DiMarco, et. al, Phrenic Nerve Pacing in a Tetraplegic Patient via Intramuscula Diaphragm Electrodes,*American Journal of Respiratory and Critical Care Medicine*, 144:1604-1606 (2002).
S.Sauermann, et. al, Computer Aided Adjustment of the Phrenic Pacemaker: Automatic Functions, Documentation, and Quality Control, *Artificial Organs*, 21(3):216-218 (1997).
B.D. Schmit, et. al, An Implantable Impedance Pneumograph Monitor for Detection of Diaphragm Contraction and Airway Obstruction During Diaphragm Pacing, *Medical & Biological Engineering & Computing*, 37:162-168 (1999).
Brian D. Schmit, et. al, Laparoscopic Placement of Electrodes for Diaphragm Pacing Using Stimulation to Locate the Phrenic Nerve Motor Points, *Transactions on Rehabilitation Engineering*, 6(4):382-390 (Dec. 1998).
W. Glenn "Diaphragm Pacing: Present Status" PACE vol. 1 p. 357-370 (1978).
Shier, D. et al, Hole's Human Anatomy & Physiology,pp. 798 (2 pages total).
Aiyar, H. et al, "Laparoscopic Implant Device for Intermuscular Electrodes," *IEEE-EMBC and CMBCC*, pp. 1167-1168, 1995.
Bernardi, L. et al, "Effect of Rosary Prayer and Yoga Mantras on Autonomic Cardiovascular Rhvthms: Comparative Study," *BMJ*, 323:22-29, Dec. 2001.
Bernardi, L. et al, "Slow Breathing Increases Arterial Baroreflex sensitivity in Patients with Chronic Heart Failure," *Circulation*,2002.
Gosselink, R. "Controlled Breathing and Dyspnea in Patients With Chronic Obstructive Pulmonary Disease," *Journal of Rehabilitaiton Research and Development*, 40(5):20-34, Supplement 2, Sep./Oct. 2003.
Jensen, A. et al, "Signal Transduction in Smooth Muscle: Airway caliber in healthy and asthmatic subjects effects of bronchial challenge and deep inspirations," *J. Appl Physiol*, 91:506-515, 2001.
Patroniti, M.D., et al "Sigh Improves Gas Exchange and Lung Volume in Patients with Acute Respiratory Distress Syndrome Undergoing Pressure Support Ventilation," *Anesthesiology*,96:788-794, 2002.
Series, F. et al, "Increasing the Functional Residual Capacity May Reverse Obstructive Sleep Apnea Sleep," 11(4):349-353, 1988.
Simon, P. et al, "Vagal Feedback in the Entrainment of Respiration to Mechanical Ventilation in Sleeping Humans," *J. App. Physiol*, 89:760-769, 2000.
Iazzo, P. ed., "Handbook of Cardiac Anatomy, Physiology, and Devices", p. 398, 2009.
Liem, L.B., "EP 101: Ventricular Tachycardia", EP Lab Digest, v.7, No. 8, Aug. 2007.
Malkin R. et al., "The Effect of Inducing Ventricular Fibrillation with 50-Hz Pacing Versus T are Stimulation on the Ability to Defibrillate", Pacing and Clinical Electrophysiology, vol. 21, issue 5, May 1998.
U.S. Appl. No. 11/246,439, filed Oct. 11, 2005 in the name of Tehrani, non-final Office Action mailed Sep. 30, 2009.
U.S. Appl. No. 11/249,718, filed Oct. 13, 2005 in the name of Tehrani, non-final Office Action mailed Apr. 18, 2008.
U.S. Appl. No. 11/249,718, filed Oct. 13, 2005 in the name of Tehrani, final Office Action mailed Apr. 1, 2009.
U.S. Appl. No. 11/249,718, filed Oct. 13, 2005 in the name of Tehrani, non-final Office Action mailed Nov. 25, 2009.
U.S. Appl. No. 11/981,800, filed Oct. 31, 2007 in the name of Tehrani et al., non-final Office Action mailed Oct. 7, 2009.
U.S. Appl. No. 10/966,421, filed Oct. 15, 2004 in the name of Tehrani, Final Office Action mailed Oct. 26, 2009.
U.S. Appl. No. 11/271,554, filed Nov. 10, 2005 in the name of Tehrani et al., non-final Office Action mailed Dec. 24, 2009.
U.S. Appl. No. 11/981,831, filed Oct. 31, 2007 in the name of Tehrani et al., non-final Office Action mailed Jan. 6, 2010.
U.S. Appl. No. 10/966,474, filed Oct. 15, 2004 in the name of Tehrani, Final Office Action mailed Jan. 21, 2010.
U.S. Appl. No. 10/966,472, filed Oct. 15, 2004 in the name of Tehrani et al., non-final Office Action mailed Feb. 23, 2010.
U.S. Appl. No. 11/526,949, filed Sep. 25, 2006 in the name of Tehrani, final Office Action mailed Mar. 19, 2010.
U.S. Appl. No. 11/271,726, filed Nov. 10, 2005 in the name of Tehrani et al., non-final Office Action mailed Mar. 31, 2010.
U.S. Appl. No. 11/271,264, filed Nov. 10, 2005 in the name of Tehrani et al., non-final Office Action mailed Mar. 30, 2010.
U.S. Appl. No. 11/271,315, filed Nov. 10, 2005 in the name of Tehrani et al., Final Office Action mailed Mar. 31, 2010.
U.S. Appl. No. 11/271,315, filed Nov. 10, 2005 in the name of Tehrani et al., non-final Office Action mailed Oct. 3, 2008.
U.S. Appl. No. 11/981,342, filed Oct. 31, 2007 in the name of Tehrani et al., non-final Office Action mailed Apr. 15, 2010.
U.S. Appl. No. 11/480,074, filed Jun. 29, 2006 in the name of Tehrani et al., Final Office Action mailed Apr. 30, 2010.
U.S. Appl. No. 10/966,421, filed Oct. 15, 2004 in the name of Tehrani, non-final Office Action mailed Jun. 9, 2010.
U.S. Appl. No. 12/080,133, filed Apr. 1, 2008 in the name of Tehrani et al., non-final Office Action mailed Jun. 10, 2010.
U.S. Appl. No. 11/246,439, filed Oct. 11, 2005 in the name of Tehrani, final Office Action mailed Jun. 29, 2010.
U.S. Appl. No. 11/249,718, filed Oct. 13, 2005 in the name of Tehrani, final Office Action mailed Sep. 14, 2010.
U.S. Appl. No. 11/526,949, filed Sep. 25, 2006 in the name of Tehrani, non-final Office Action mailed Oct. 5, 2010.
U.S. Appl. No. 11/981,342, filed Oct. 31, 2007 in the name of Tehrani et al., final Office Action mailed Oct. 7, 2010.
U.S. Appl. No. 11/271,554, filed Nov. 10, 2005 in the name of Tehrani et al., final Office Action mailed Jan. 31, 2011.
U.S. Appl. No. 11/981,800, filed Oct. 31, 2007 in the name of Tehrani et al., final Office Action mailed Jan. 20, 2011.
U.S. Appl. No. 10/966,421, filed Apr. 8, 2008 in the name of Tehrani, final Office Action mailed Feb. 17, 2011.
U.S. Appl. No. 11/480,074, filed Jun. 29, 2006 in the name of Tehrani et al., non-final Office Action mailed Mar. 16, 2011.
U.S. Appl. No. 10/966,474, filed Oct. 15, 2004 in the name of Tehrani et al., non-final Office Action mailed Mar. 30, 2011.
U.S. Appl. No. 11/981,727, filed Oct. 31, 2007 in the name of Tehrani et al., non-final Office Action mailed Apr. 4, 2011.
U.S. Appl. No. 11/249,718, filed Oct. 13, 2005 in the name of Tehrani, non-final Office Action mailed Apr. 1, 2011.
U.S. Appl. No. 11/271,726, filed Nov. 10, 2005 in the name of Tehrani et al., non-final Office Action mailed Apr. 4, 2011.
U.S. Appl. No. 11/271,264, filed Nov. 10, 2005 in the name of Tehrani et al., final Office Action mailed Apr. 7, 2011.
Heinzer, R., et al, "Lung Volume and Continuous Positive Airway Pressure Requirements in Obstructive Sleep Apeau" *American Journal of Respiratory and Critical Care Medicine*, vol. 172, pp. 114-117, 2005.
DiMarco, A F., "Combined Intercostal and Diaphragm Pacing to Provide Artificial Ventilation in Patients With Tetraplegia" *Arch Phys Med Rehabil*, vol. (86), pp. 1200-1207, 2005.
Dunn, R., "Diaphragm and Accessory Respiratory Muscle Stimulation Using Intramuscular Electrodes" *Arch Phys Med Rehabil*, vol. 76, pp. 266-271, 1995.
Glenn, W., et al. "Diaphragm Pacing"*Journal of Thoracic and Cardiovascular Surgery*, vol. 75:2, pp. 273-281, 1978.
U.S. Appl. No. 11/271,726, filed Nov. 10, 2005 in the name of Tehrani et al., Notice of Allowance mailed May 18, 2011.
U.S. Appl. No. 11/271,264, filed Nov. 10, 2005 in the name of Tehrani et al., Notice of Allowance mailed May 20, 2011.
"Quadripolar Pacing Addresses Issues Without Moving Leads," *Diagnostic & Invasive Cardiology*, 1 page, Jun. 1, 2010, Scranton Gillette Communications.
Abraham, W., "Advances in Heart Failure Therapy in the Primary Care Context," *Medscape Family Medicine/Primary Care*, 7 pages, 2004.
Arzt, M. et al, "Treatment of Sleep Apnea in Heart Failure," *AJRCCM*, 36 pages, Mar. 9, 2006.

Boston Scientific, "Diaphragm Stimulation During Daily LV Lead Impedance Measurements", Product Education Brochure, 2 pages, Sep. 26, 2008.

Bradley, T.D. et al, "Sleep Apnea and Heart Failure, Part I: Obstructive Sleep Apnea," *Circulation*, pp. 1671-1678, Apr. 1, 2003.

Fessler, H.E., "Heart-Lung Interactions: Applications in the Critically Ill," *Eur. Respir. J.*, vol. 10, pp. 226-237, 1997.

Fichter, J. et al, "Sleep-Related Breathing Disorders are Associate with Ventricular Arrhythmias in Patients with an Implantable Cardioverter-Defibrillator," *Chest*, vol. 122, pp. 558-561, Aug. 2002.

Garrigue, S. et al "Sleep Apnea: A New Indication for Cardiac Pacing?," *Pace*, vol. 27, pp. 204-211, Feb. 2004.

Hayano, J. et al "Respiratory Sinus Arrhythmia: A Phenomenon Improving Pulmonary Gas Exchange and Circulatory Efficiency," *Circulation*, vol. 94, pp. 842-847, 1996.

Hennersdorf. M.G. et al. "Chemoreflexsensitivity in Chronic Heart Failure Patients," *European Journal of Heart Failure*, vol. 3, pp. 679-684, 2001.

Ishii, K. et al "Effects of Bilateral Transvenous Diaphragm Pacing on Hemodynamic Function in Patients after Cardiac Operations," *J Thorac Cardrovasc Surg*, vol. 100, pp. 108-114, 1990.

Javaheri, S. et al, "Sleep Apnea in 81 Ambulatory Male Patients with Stable Heart Failure: Types and Their Prevalences, Consequences, and Presentations," *Circulation*, vol. 97, pp. 2154-2159, 1998.

Kohnlein, T. et al, "Central Sleep Apnea Syndrome in Patients with Chronic Heart Disease: a Critical Review of the Current Literature," *Thorax*, vol. 57, pp. 547-554, 2002.

Krachman, S. et al "Comparison of Oxygen Therapy with Nasal Continuous Positive Airway Pressure on Cheyne-Stokes Respiration During Sleep in Congestive Heart Failure," *Chest*, vol. 116, pp. 1550-1557, Dec. 1999.

LaFond, C. et al "Impact of CPAP on Asthmatic Patents with Obstructive Sleep Apnoea," *Eur Respir J*, vol. 29, pp. 307-311, 2007.

Lanfranchi, P.A. et al, "Prognostic Value of Nocturnal Cheyne-Stokes Respiration in Chronic Heart Failure," *Circulation*, pp. 1435-1440, 1999.

Leung, R. et al, "Sleep Apnea and Cardiovascular Disease," *Am J Respir Crit Care Med*, vol. 164, pp. 2147-2165, 2001.

Mathew, O., "Effects of Transient Intrathoracic Pressure Changes (hiccups) on Systemic Arterial Pressure," *J Appl Physiol*, vol. 83, pp. 371-375, 1997.

Norton, J., "Toward Consistent Definitions for Preload and Afterload," *Advan in Physiol Edu*, vol. 25, pp. 53-61, Mar. 2001.

Peters, J. et al, "Negative Intrathoracic Pressue Decreases Independently Left Ventricular Filling and Emptying," *American Physiological Society*, pp. H120-H131, 1989.

Pinsky, M. "Cardiovascular Issues in Respiratory Care," *Chest*, vol. 128, pp. 592-597, Nov. 2005.

Schultz, R. et al "Nocturnal Periodic Breathing in Primary Pulmonary Hypertension," *Eur Respir J*, vol. 19, pp. 658-663, 2002.

Series, F. et al, "Assessment of Upper Airway Stabilizing Forces with the Use of Phrenic Nerve Stimulation in Conscious Humans," *J Appl Physiol*, vol. 94, pp. 2289-2295, 2003.

Sorli, J. et al., "Ventilatory Assist Using Electrical Stimulation of AJdominal Muscles," *IEEE Transactions of Rehabilitation Engineering*, vol. 4, No. 1, pp. 1-6, Mar. 1996.

Van Houwelingen, K. et al "The Sleep Apnoea Syndromes," *European Heart Journal*, vol. 20, pp. 858-866, Jun. 1999.

Viasys Healthcare, "Ventilation Requires Perfect Balance", SensorMedics® 3100A HFOV, VIASYS Healthcare Brochure, 2 pages.

Wolk, R. et al "Sleep-Disordered Breathing and Cardiovascular Disease," *Circulation*, vol. 108, pp. 9-12, Jul. 2003.

Yim, S. et al "Continuous Positive Airway Pressure for Asthma: Not a Big Stretch?," *Eur Respir J*, vol. 29, pp. 226-228, 2007.

\* cited by examiner

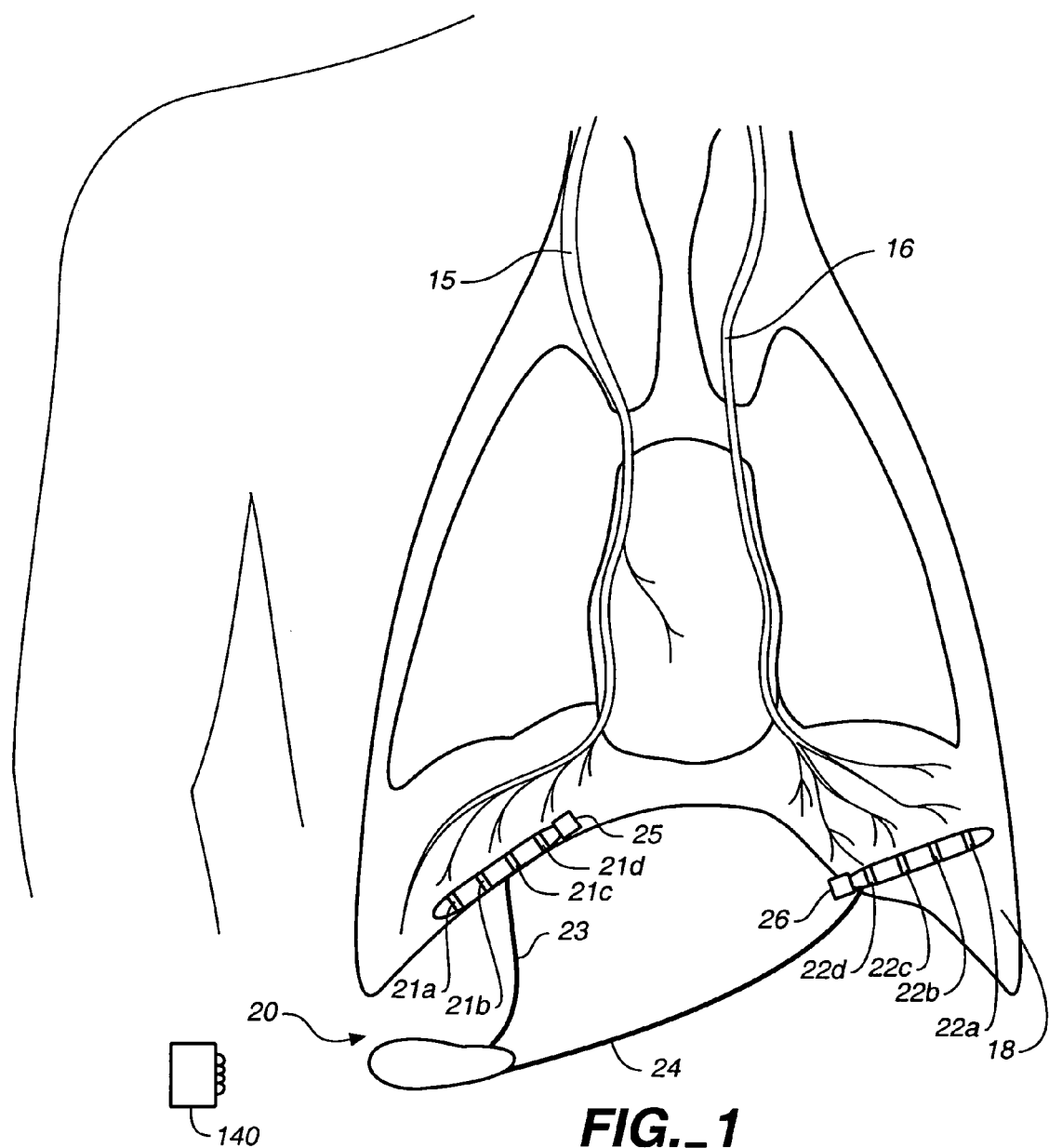
FIG._1

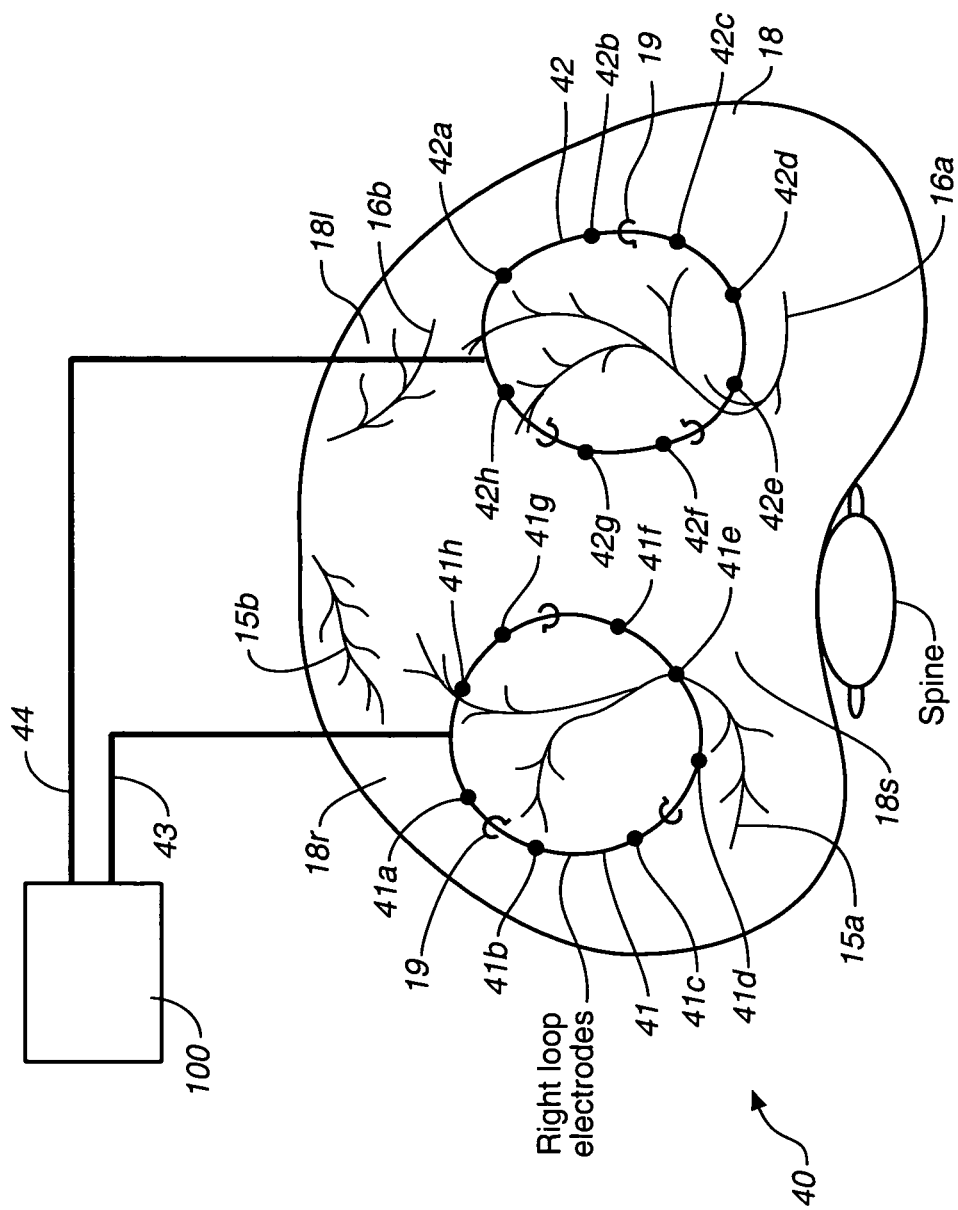
FIG._2

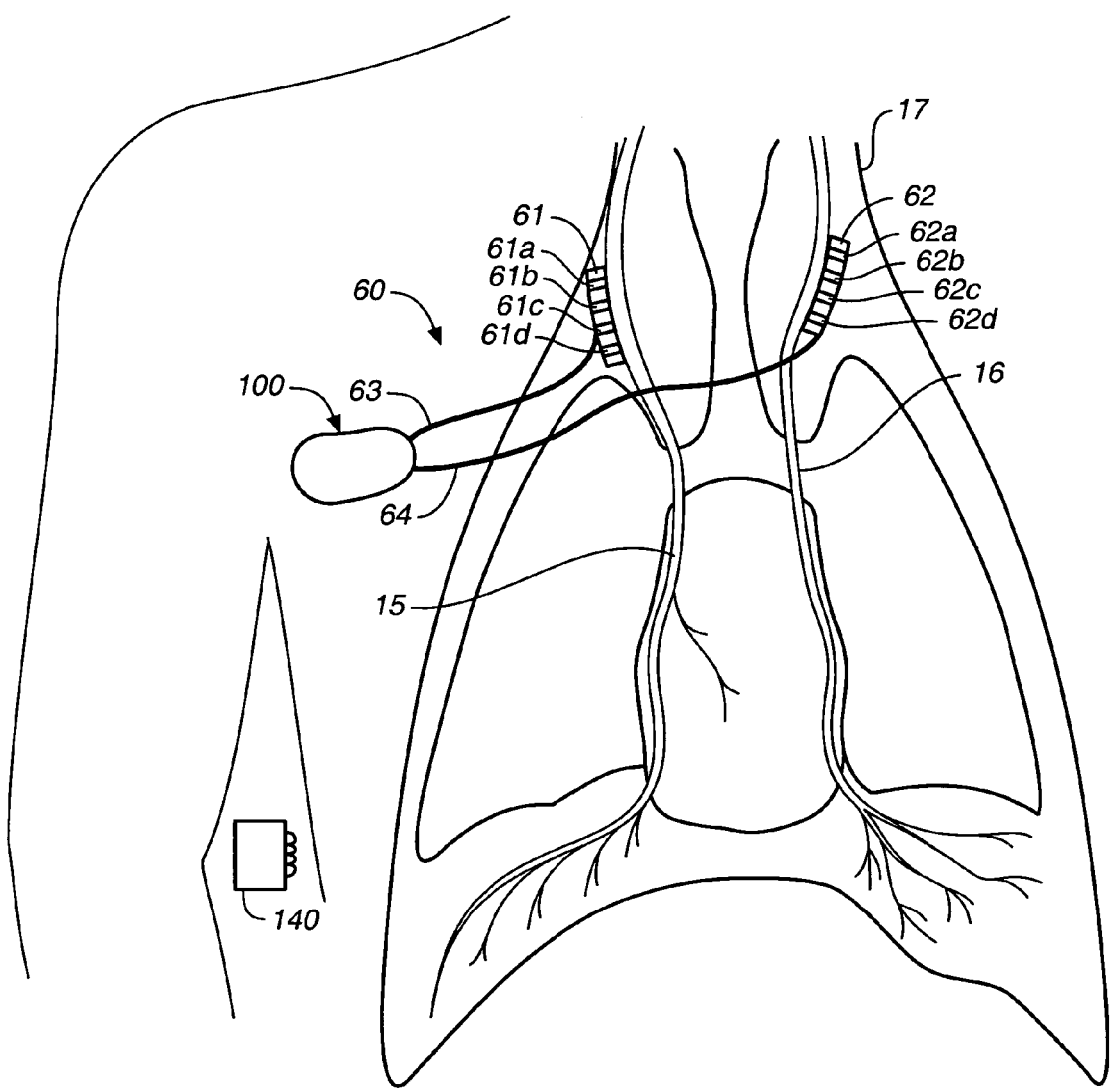
FIG._3

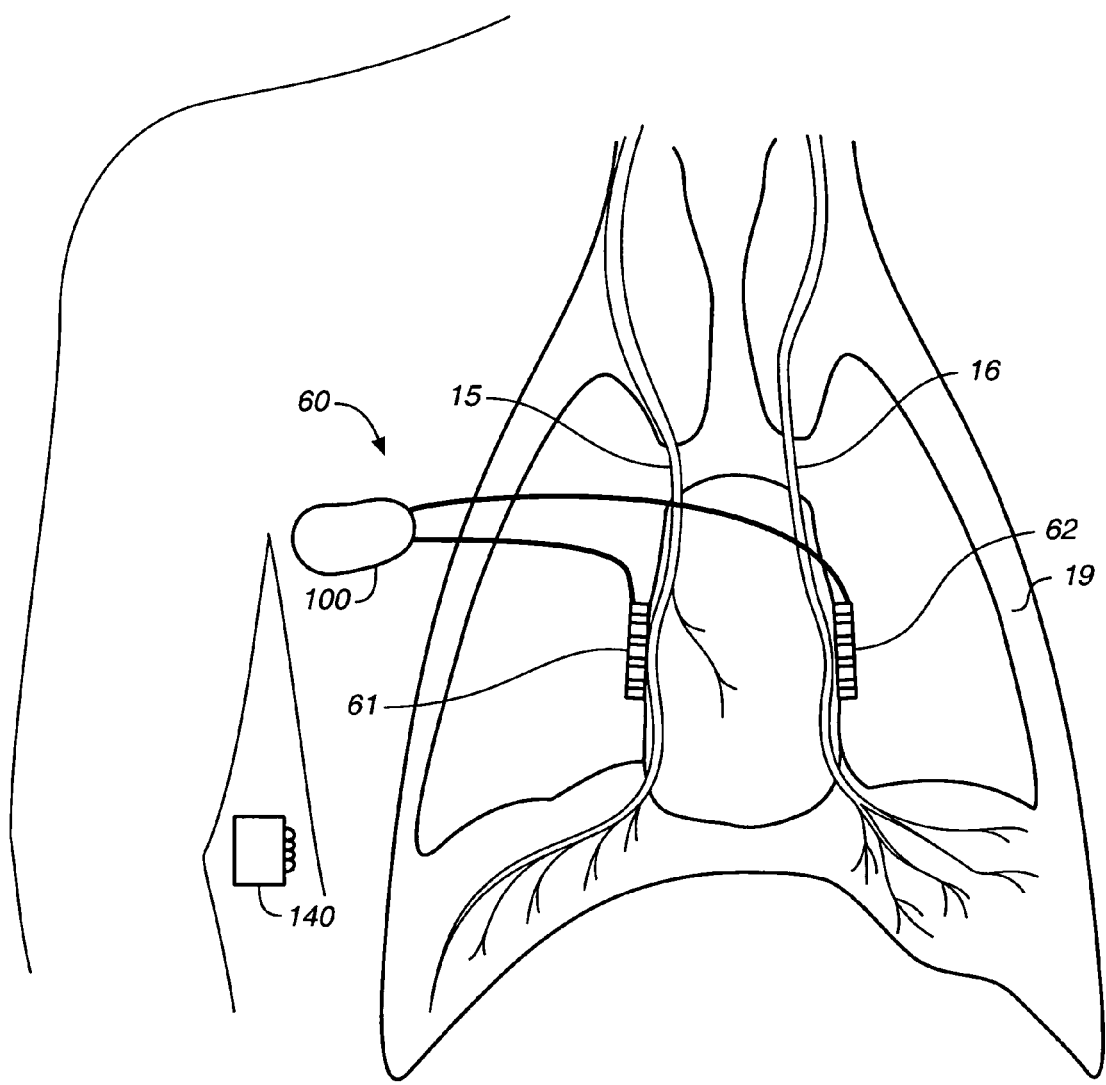
FIG._4

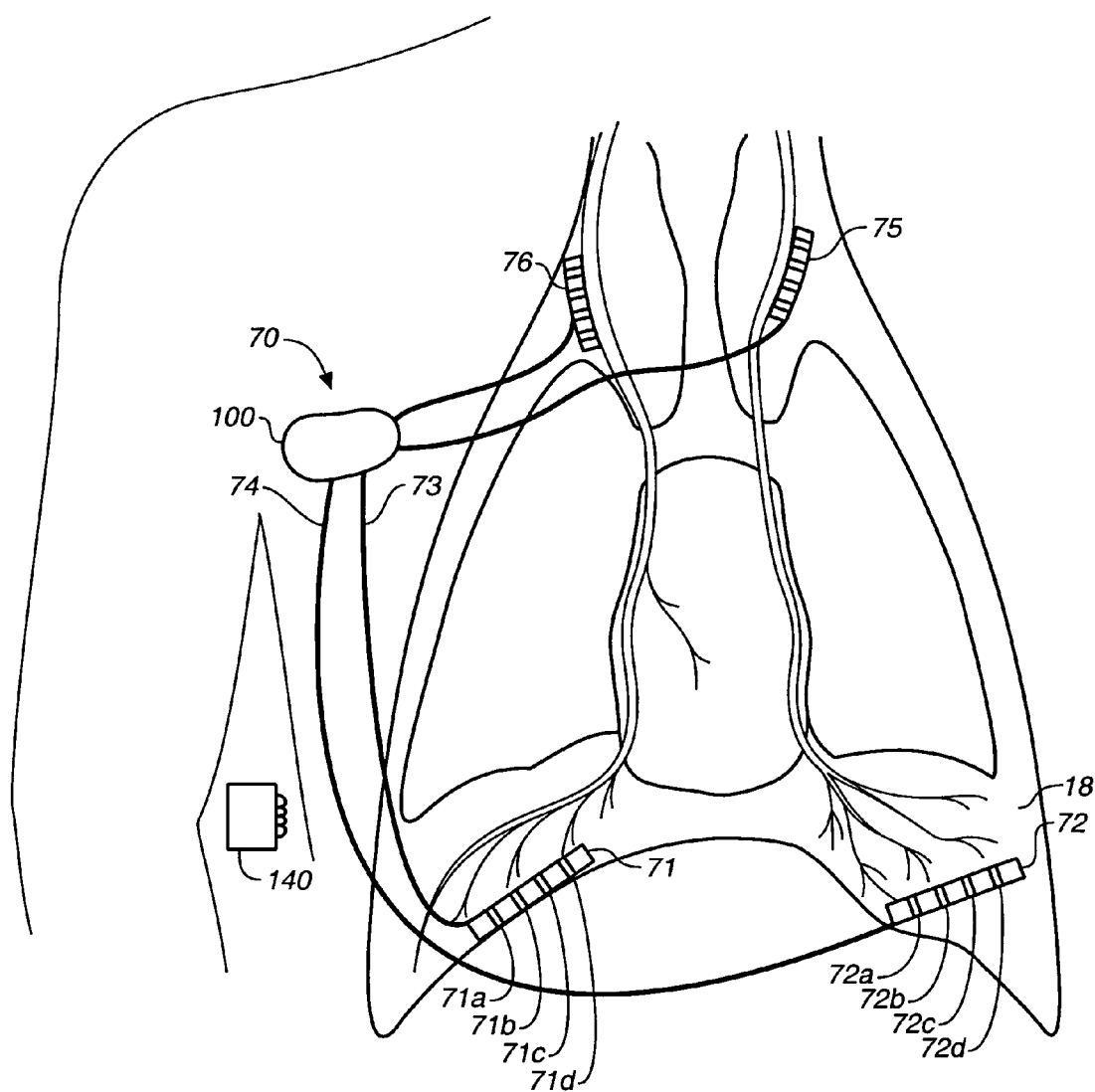
FIG._5

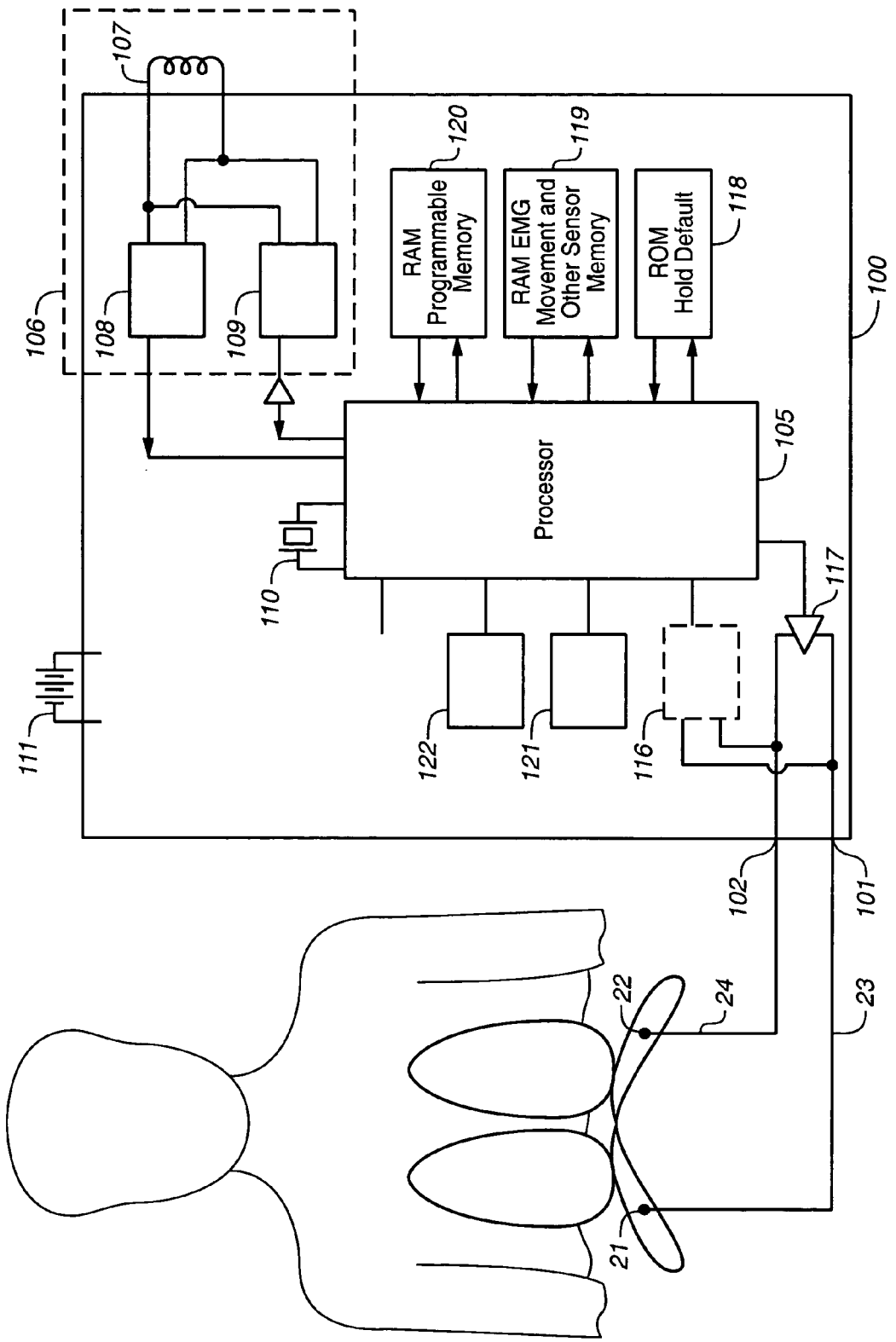
FIG._6

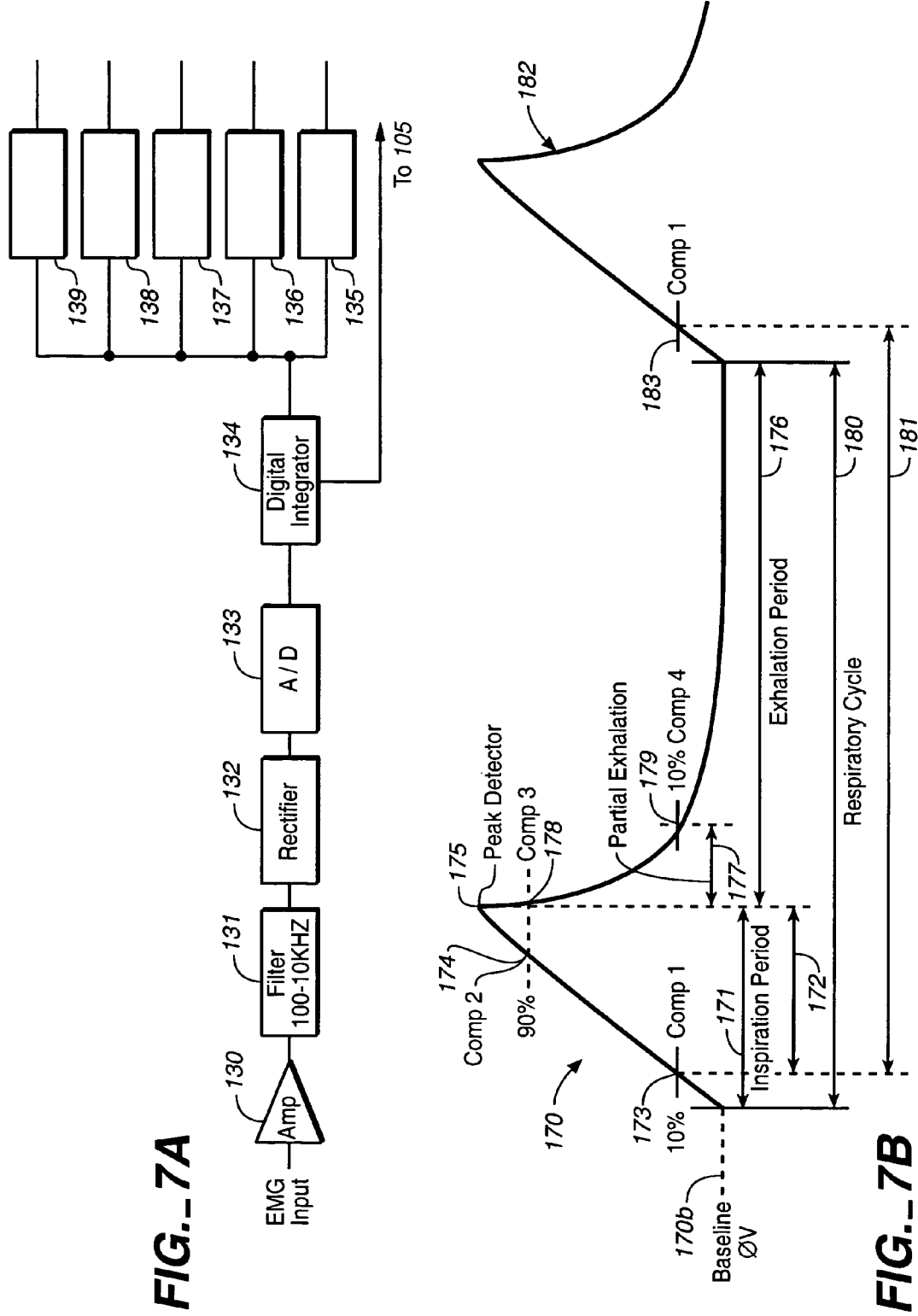

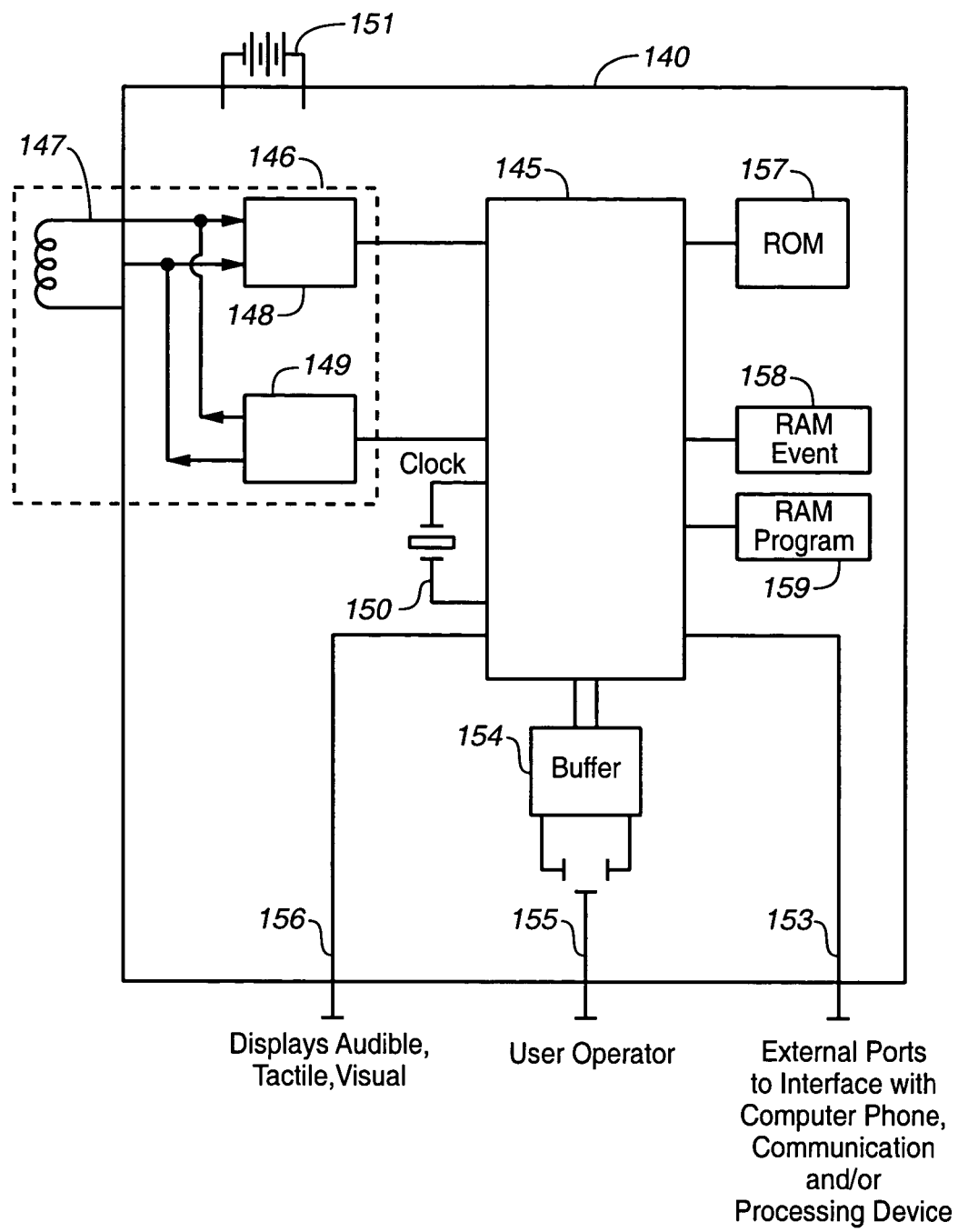
FIG._8

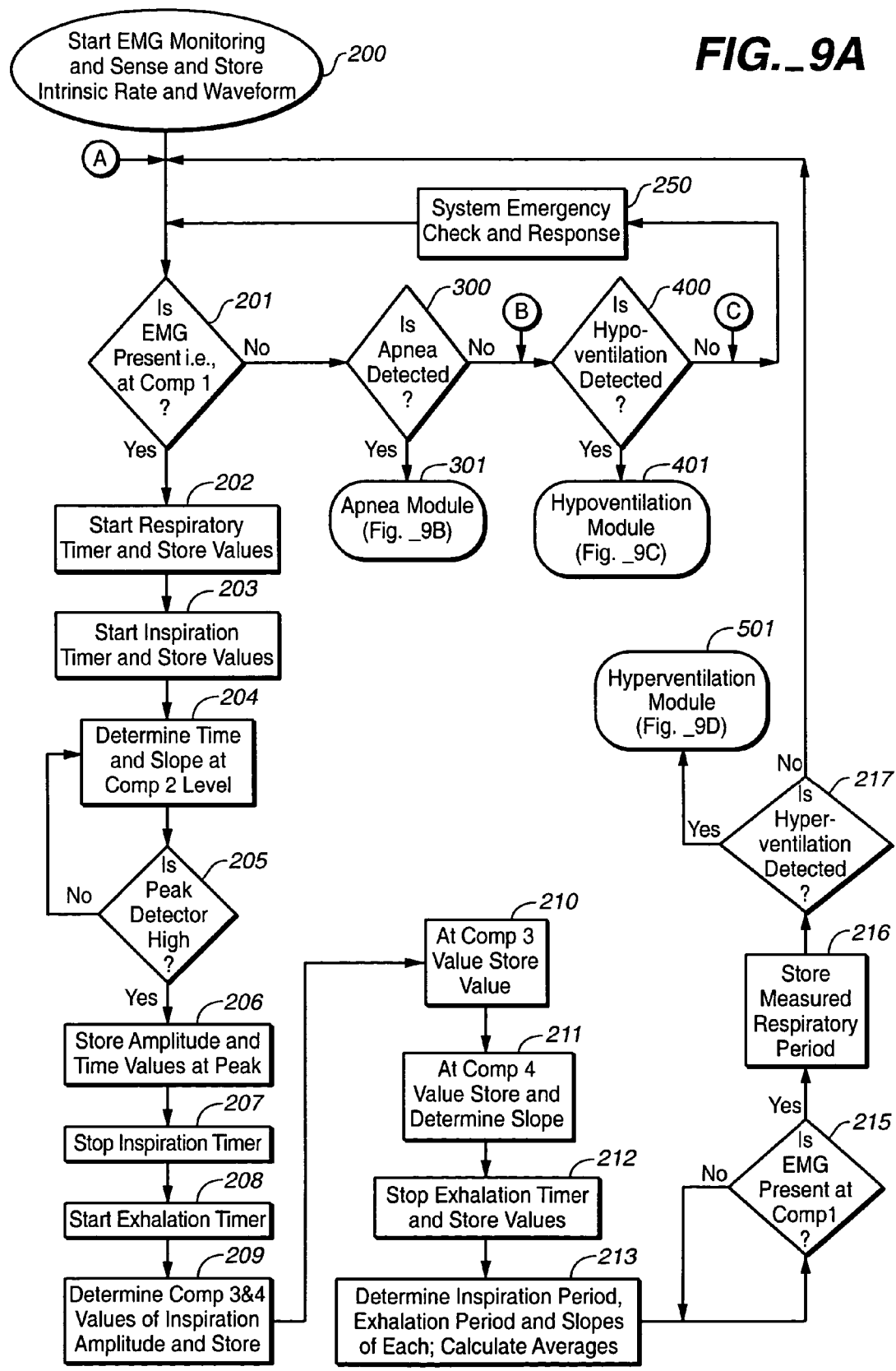
FIG._9A

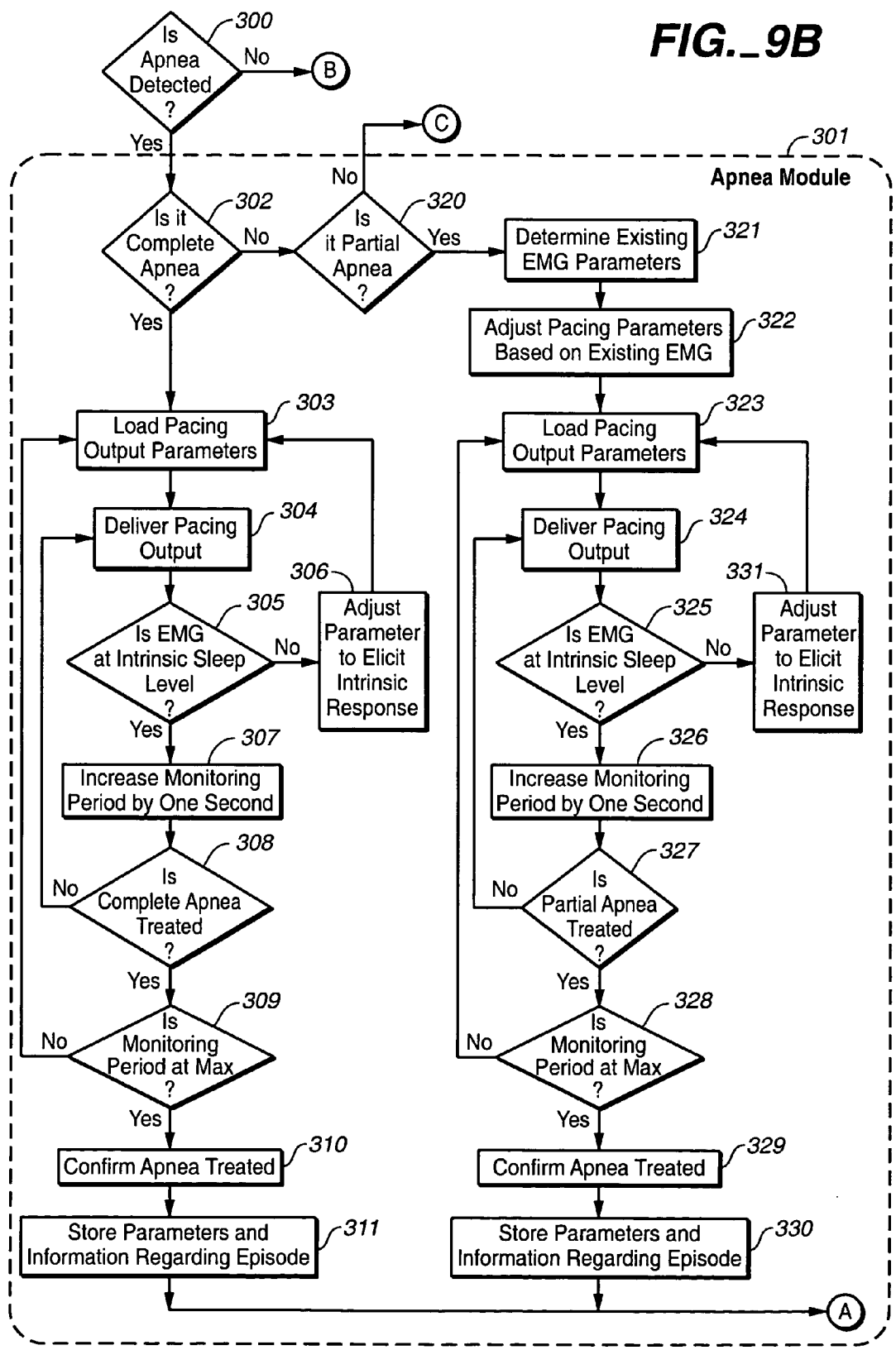
FIG._9B

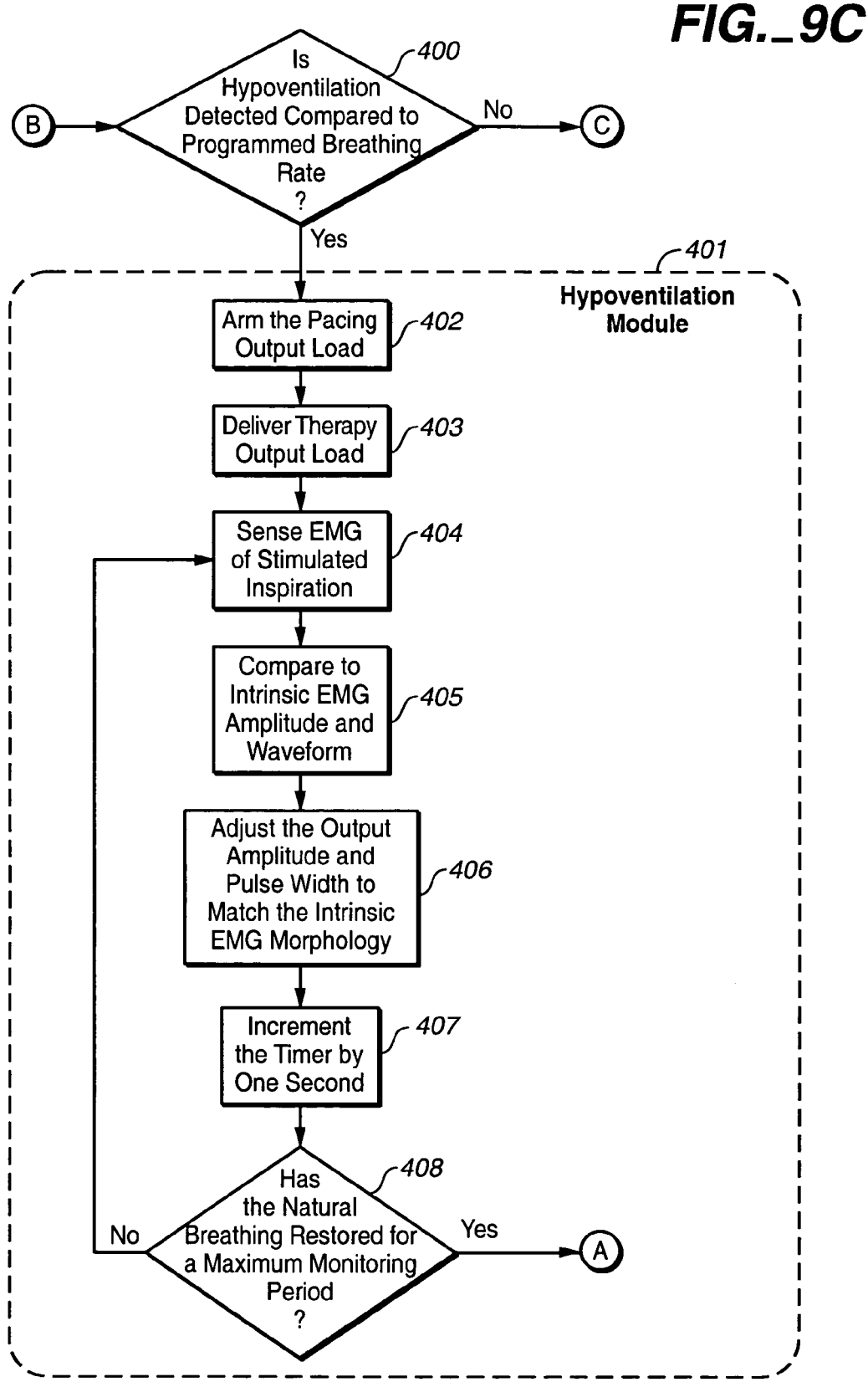
FIG._9C

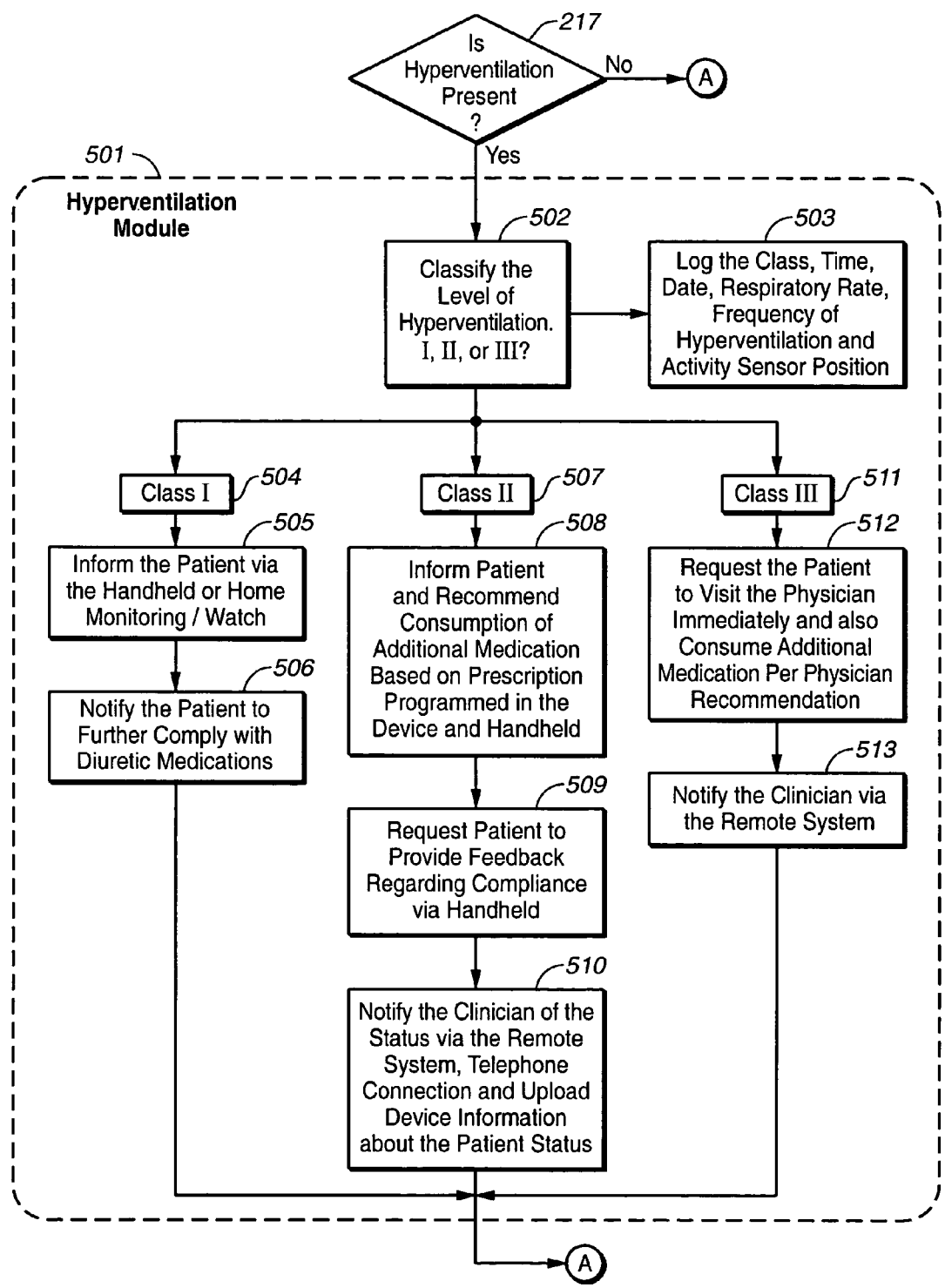
FIG._9D

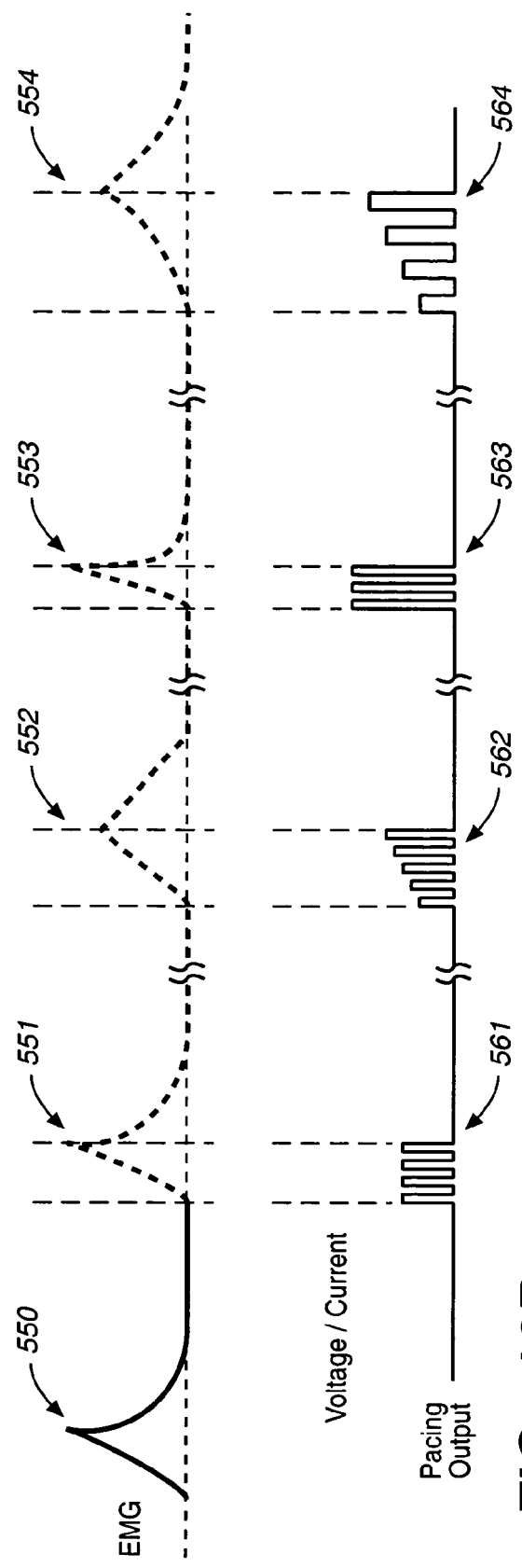

though to stimulate the diaphragm to manage breathing.

BREATHING DISORDER DETECTION AND THERAPY DELIVERY DEVICE AND METHOD

FIELD OF THE INVENTION

The invention relates to a device and method for detection, diagnosis and treatment of breathing insufficiencies or irregularities and to the management of pulmonary rhythm. Such irregularities may include, for example, hyperventilation, hypoventilation and apnea. The invention also relates to stimulating respiration in response to detecting hypoventilation or apnea.

BACKGROUND OF THE INVENTION

Breathing insufficiencies and irregularities may occur in conjunction with or as a result of a variety health related disorders and may further cause or exacerbate health disorders. Such breathing insufficiencies and irregularities may include, for example, hyperventilation, hypoventilation, apnea, and other related breathing disorders. Hyperventilation, which results in hyperoxia, is a condition in which the respiratory rate is pathologically high or is above a desired rate. Hyperventilation may occur due to pulmonary edema or excess fluid built up in the lungs and may ultimately result in apnea episodes. Hypoventilation is a condition in which the respiratory rate is pathologically low or below a desired rate. Apnea (absence of breathing) is a breathing disorder most typically occurring during sleep that can result from a variety of conditions. Sleep apnea typically results in some sort of arousal or wakefulness following cessation of breathing.

Sleep disordered breathing disorders include two types of sleep apnea: obstructive sleep apnea (partial apnea or obstructive apnea) and central sleep apnea. Obstructive sleep apneas result from narrowing of the pharynx with out-of-phase breathing in an effort to create airflow, whereas central sleep apnea arises from reductions in central respiratory drive. During obstructive sleep apnea, respiratory effort increases. In central sleep apnea, respiratory movements are absent or attenuated but in phase.

Disordered breathing may contribute to a number of adverse cardiovascular outcomes such as hypertension, stroke, congestive heart failure, and myocardial infarction. Sleep-related breathing disorders, especially central sleep apnea, have been found to have a relatively high prevalence in patients with heart failure and may have a causative or influencing effect on heart failure. In about 50% of patients with stable congestive heart failure, there is an associated sleep disordered breathing, predominantly central sleep apnea with a minority having obstructive sleep apnea. Furthermore, sleep related breathing disorders are believed to be physiologically linked with heart failure. Central sleep apnea is a known risk factor for diminished life expectancy in heart failure. It is also believed that in view of this link, treatment aimed at relieving sleep related breathing disorders may improve cardiovascular outcomes in patients with heart failure.

Pulmonary edema, a condition in which there is excess fluid in the lungs and often found in heart failure patients, is believed in some circumstances to lead to hyperventilation and hyperoxia or apnea. Most heart failure patients with central sleep apnea, when lying flat, tend to have central fluid accumulation and pulmonary congestion, which stimulates vagal irritant receptors in the lungs to cause reflex hyperventilation. Central Sleep Apneas usually are initiated by reduction in $PCO_2$ resulting from the increase in ventilation. When $PCO_2$ falls below the threshold level required to stimulate breathing, the central drive to respiratory muscles and airflow cease or diminish significantly and apnea (or attenuated breathing) ensues until the $PCO_2$ rises again above the threshold required to stimulate ventilation. Often spontaneous arousal occurs with apnea.

Currently a number of methods are used to treat sleep apnea. For example, supplemental oxygen such as, e.g., with a nasal ventilator, has been used to relieve symptoms of sleep apnea. Non-invasive airway pressure including continuous positive airway pressure (CPAP), bivalve and adaptive pressure support servo-ventilation have been used to treat central sleep apnea and obstructive sleep apnea with varying results. Another method to treat central sleep apnea is using aggressive diuresis to lower cardiac filling and beta-blocker and angiotensin-converting enzymes. However, this treatment does not lead to an optimum therapy since excessive use of diuretics leads to renal complications and patient discomfort.

A method and apparatus for treatment of obstructive sleep apnea has been proposed where an implantable pulse generator stimulates a nerve in the upper airway tract of a patient to elicit a contraction by an innervated muscle through the provision of electrical stimuli. The stimulator is intended to treat the obstructed airway passage to permit breathing. The pulse generator is attached to electrodes placed on the patient's diaphragm for sensing the respiratory effort of a patient whereupon the stimulation is adjusted. The method and apparatus do not provide a satisfactory treatment of central sleep apnea.

Phrenic nerve stimulation has been used to stimulate the diaphragm throughout an overnight period to treat sleep apnea. The device used was turned on at night to stimulate the nerve continuously and then turned off during the day. However, this device was not adapted for situations where patients would breath spontaneously.

Accordingly it would be desirable to provide a method and apparatus for treating breathing disorders such as apnea, and hypoventilation, and especially central sleep apnea. Furthermore it would be desirable to provide treatments for breathing related disorders related pulmonary edema and conditions in heart failure patients.

SUMMARY OF THE INVENTION

The present invention provides a method and apparatus for treating breathing disorders by sensing the respiratory parameters of the diaphragm and stimulating an associated body organ or tissue to control movement of the diaphragm and thus manage respiration. In a variation, the method and apparatus provide stimulation to the diaphragm to elicit diaphragm movement to cause respiration when respiration ceases or falls below a threshold level.

One embodiment is a device comprising: a sensor for sensing information corresponding to respiratory effort of the diaphragm and a processor for processing the sensed information and delivering electrical stimulating pulses to the associated body organ or tissue based on sensed information. The processor may further determine stimulation parameters based at least in part on sensed information. Also, the processor may determine when to cease stimulation by determining when the body resumes normal respiratory function.

The respiratory effort may be sensed, for example, by sensing the phrenic nerve activity and/or the EMG of the diaphragm, or by detecting movement of the diaphragm or chest. Respiration by the diaphragm may be stimulated by electrically stimulating the phrenic nerve and/or by stimulating the diaphragm muscle.

A number of different parameters may be programmed into the processor to determine if certain breathing disorders are present, and when and how to stimulate respiration, and when to stop or modify stimulation.

Phrenic nerve or EMG activity sensed may include, for example, amplitude, frequency, and waveform to determine central respiratory efforts, the absence, a decrease in amplitude, abnormalities in frequency and/or amplitude, or waveform morphology of which may indicate the onset of apnea, hyperventilation, or hypoventilation. The nerve activity may be compared to predetermined activity levels or patient historical activity. Similarly, diaphragm EMG amplitude, frequency, waveform morphology and history may be used to determine apnea, hyperventilation and hypoventilation. For example, the nerve activity at the onset of sleep or after a given time in a reclining position, may be used as a baseline for comparison.

An awake sinus zone may be defined as a respiratory rate or range of rates programmed into the device for a specific patient when awake, where the respiratory rate is considered normal and intrinsic. A preprogrammed EMG amplitude or range may define a normal range in this state. A sleep sinus may be defined as a respiratory rate or range of rates programmed into the device for a specific patient when asleep where the respiratory rate is considered normal and intrinsic. A preprogrammed EMG amplitude or range may define a normal range in this state. The device may be programmed to match the EMG rate and amplitude to a normal rate and amplitude by auto adjusting the pace output.

Hypoventilation may be detected where the respiratory rate or frequency falls below a programmed rate. Hyperventilation may be detected when the respiratory rate or frequency is above a programmed rate. Complete apnea or central apnea is defined as a condition where there is no effective EMG signal or phrenic nerve signal, i.e. where there is no effective or significant physiological response. Frequently, a hyperventilation episode is followed by loss of diaphragm EMG or phrenic nerve activity. The device may be programmed to first detect the hyperventilation and wait for a preprogrammed time to be considered apnea. For example the time may be set to 10-20 seconds of lost EMG after a hyperventilation episode to detect complete apnea. Partial apnea or obstructive sleep apnea is defined to be present when the EMG or phrenic nerve activity is attenuated and may be detected when the amplitude drops below a programmed amount. For example such amount may be based on the EMG or phrenic nerve amplitude dropping a percentage, e.g. 50% of the Sleep Sinus EMG amplitude. Also the phase of the respiratory cycles in partial apnea may be determined or compared to an in phase cycle. An out of phase or arrhythmic cycle may also be used to detect partial apnea.

In addition, position sensors may be used to determine degree of patient reclining or standing, e.g., in increments of degrees. Information from the position sensor may be used as a tool to match respiratory activities and patterns to the position of the patient. Accelerometer information may be used to determine information regarding patient's physical activity, e.g., to match/compare to the respiratory patterns and activities and collect data on related patient activities, respiratory activities, and create or adjust a treatment plan based thereon, (e.g., modification of diuretics or ACE inhibitors). Accelerometer sensors may also be used to determine information regarding movement pattern of the diaphragm muscles, intercostal muscles, and rib movement and thus determine overall respiratory activity and patterns.

According to an embodiment, a stimulator includes an implantable controller coupled through leads to electrodes to be implanted on the diaphragm in the vicinity of the phrenic nerve branches. The electrodes may sense either nerve activity or EMG signals of the diaphragm. The stimulator may further include a pulse generator configured to deliver stimulating pulses, either to the same electrodes used for sensing or to additional stimulation electrodes. The stimulation electrodes may also be placed adjacent the phrenic nerve at some point along its length to provide stimulation pulse to the nerves, which in turn enervate the diaphragm muscle causing contractions and resulting respiration. Alternatively the electrodes may be placed on the phrenic nerve for both sensing and stimulation.

Stimulation of respiration may be initiated when "no" or "attenuated" respiratory activity has been present or detected for a time period (when apnea is detected). The time period may be pre-programmed for a specific patient by the physician, as otherwise preset, or as determined a program in the treatment device. The device may be programmable for other breathing disorders, allowing slow or fast inspiration and visa versa allowing slow or fast expiration. For example, based on programmed parameters of the activity sensor, for patients suffering from hypoventilation, the inspiration rate may be increased or decreased based on the level of activity.

Pacing starts at given intervals. In one embodiment the interval time is initially about 10 seconds. The interval is slowly increased from 11 seconds to about 15 seconds. If the patient does not breath on their own, the pacing begins again at 10-second intervals and this is repeated. If the patient begins breathing on their own, typically where the $Po_2$ and $PCO_2$ levels are normalized and the brain resumes sending nerve stimulation. The system then returns to the mode where it is sensing respiratory effort.

An additional feature of the invention may include a patient self-management module. The module can be an external device configured to telemetrically communicate with the implanted device. The module is configured to communicate information with the patient based on what is received from the implantable device. The information may also be communicated with a provider who can upload information regarding the status of the patient including urgent interventions. The device may include, paging, email, fax or other communication capabilities that can send information to a clinician. The device can be worn or carried with the patient while the patient is away from home. The device may be used to prompt the patient to comply with life-style and medication based on programmed parameters by the provider. The device may require the patient to interact with the device confirming compliance. The provider may receive information on patient compliance.

The information that may be downloaded for sleep apnea treatment may include, e.g., detection rate, detection amplitude, pacing therapy amplitude, pacing pulse width, pacing frequency or other stimulation waveform morphology. This information may be used to calibrate device detection and therapy parameters.

The information that may be downloaded for pulmonary edema management (e.g., of hyperventilation rate and frequency of occurrence) may include the detections rate, detection amplitude, ventilation waveform morphology including slopes and surface of inspiration waveform, slopes and surface area of exhalation waveform, recorded respiratory waveform information in conjunction with activity and position sensors information. A provider may use the information in developing an optimum treatment plan for the patient including drug titrations for diuretic management as well as if patient is in need of urgent attention leading to hospitalization, which is a frequent occurrence with heart failure patients dealing with pulmonary edema. The patient compliance information may also be used for understanding the drug regimen effectiveness if patient complies or educate the patient when there is lack of compliance with the therapy plan.

DETAILED DESCRIPTION OF THE DRAWINGS

FIG. 1 illustrates a sleep breathing disorder treatment device in accordance with the invention placed on the diaphragm.

FIG. 2 illustrates an electrode assembly in accordance with the invention implanted on the abdominal side of the diaphragm.

FIG. 3 illustrates a sleep breathing disorder treatment device in accordance with the invention placed on the phrenic nerves.

FIG. 4 illustrates a sleep breathing disorder treatment device in accordance with the invention placed on the diaphragm and phrenic nerves.

FIG. 5 illustrates a sleep breathing disorder treatment device in accordance with the invention placed on the phrenic nerves.

FIG. 6 illustrates a processor unit of a sleep breathing disorder treatment device in accordance with the invention.

FIG. 7A is a schematic of a signal processor of the processor unit in accordance with the invention.

FIG. 7B is an example of a waveform of an integrated signal processed by the signal processor of FIG. 7A.

FIG. 8 is a schematic of an external device of a stimulator in accordance with the invention.

FIGS. 9A-9D are flow diagrams of the operation of a stimulator in accordance with the invention.

FIG. 9B is a flow diagram of sleep apnea treatment with a stimulator in accordance with the invention.

FIG. 9C is a flow diagram of hypoventilation treatment with a stimulator in accordance with the invention.

FIG. 9D is a flow diagram of hyperventilation treatment with a stimulator in accordance with the invention.

FIGS. 10A-10B are an illustration of a variety of stimulation bursts with different parameters (FIG. 10B) corresponding to different resulting EMG signals (FIG. 10A).

DETAILED DESCRIPTION OF THE INVENTION

FIG. 1 illustrates a stimulator 20 comprising electrode assemblies 21, 22, each comprising a plurality of electrodes 21a-d and 22a-d respectively. The electrode assemblies 21, 22 are implanted in the diaphragm muscle so that one or more of electrodes 21a-d and of electrodes 22a-d are approximately adjacent to one or more junctions of the phrenic nerves 15, 16, respectively, with the diaphragm 18 muscle. The electrode assemblies 21, 22 sense and pace at the diaphragm muscle. They are implanted laparoscopically through the abdomen and into the muscle of the diaphragm 18 with needles or other similar devices. The electrode assemblies 21, 22 may be anchored with sutures, staples, or other anchoring mechanisms typically used with implantable EMG electrodes. The leads 23, 24 coupling the electrode assemblies 21, 22 to the control unit 100 are then routed subcutaneously to the side of the abdomen where a subcutaneous pocket is created for the control unit 100. The electrode assemblies 21, 22 are each flexible members (such as neurostimulation leads) with electrodes 21a-d, assembled about 5-20 mm apart from one another and electrodes 22a-d assembled about 5-20 mm apart from one another. The electrode assemblies 21, 22 are coupled via leads 23, 24 to control unit 100. The control unit 100 is configured to receive and process signals corresponding to sensed nerve activity, and/or EMG of the diaphragm 18, to determine the respiratory parameters of the diaphragm 18 as described in more detail herein with reference to FIGS. 6, 7A-7B and 9A-9D.

The electrodes assemblies 21, 22 are coupled via leads 23, 24 to input/output terminals 101, 102 of a control unit 100. The leads 23, 24 comprise a plurality of electrical connectors and corresponding lead wires, each coupled individually to one of the electrodes 21a-d, 22a-d. The control unit 100 is implanted subcutaneously within the patient, for example in the chest region on top of the pectoral muscle. The control unit 100 is configured to receive sensed nerve electrical activity from the electrode assemblies 21, 22, corresponding to respiratory effort of a patient. The control unit 100 includes a processor 105 (FIG. 6) that delivers stimulation to the nerves 15,16 or diaphragm 18 in response to a sensed degree or absence of diaphragm respiratory effort as determined and processed by the processor 105 and control unit 100 as described in more detail herein with reference to FIGS. 6, 7A-7B, 8 and 9A-9D.

The stimulator 20 also comprises movement detectors 25, 26, in this example, strain gauges included with the electrode assemblies 21, 22 respectively and electrically connected through leads 23, 24 to the control unit 100. The movement detectors 25, 26 detect movement of the diaphragm 18 and thus the respiratory effort exerted by the diaphragm 18. The movement detectors 25, 26 sense mechanical movement and deliver a corresponding electrical signal to the control unit 100 where the information is processed by the processor 105. The movement may be used to qualify the electrical phrenic nerve or EMG signal sensed by the device to confirm inspiration or exhalation is occurring, e.g., by matching mechanical and electrical activities of the diaphragm.

Electrodes may be selected from the plurality of electrodes 21a-d and 22a-d (or electrodes 41a-h, 42a-h, 61a-d, 62a-d, 71a-d, 72a-d in the other examples described herein) once implanted, to form bipolar or multipolar electrode pairs or groups that optimize the stimulation response. Such desired response may include tidal volume, breathing rate and the slopes of the inhalation and exhalation curves. For example, a timed series of pulses may be used to create a desired respiratory inhalation and/or exhalation period. Testing the response may be done by selecting a bipolar electrode pair from two of the multiple electrodes in an assembly or any other combination of electrodes to form at least one closed loop system, by selecting sequence of firing of electrode groups and by selecting stimulation parameters. The electrodes may be selected by an algorithm programmed into the processor that determines the best location and sequence for stimulation and/or sensing nerve and/or EMG signals, e.g., by testing the response of the electrodes by sensing respiratory effort in response to stimulation pulses. Alternatively, the selection process may occur using an external programmer that telemetrically communicates with the processor and instructs the processor to cause stimulation pulses to be delivered and the responses to be measured. From the measured responses, the external programmer may determine the optimal electrode configuration, by selecting the electrodes to have an optimal response to a bipolar or multipolar delivery of stimulation.

FIG. 2 illustrates a diaphragm electrode assembly 40 in accordance with the invention for placement on the diaphragm 18 for sensing and/or stimulation of the diaphragm and/or phrenic nerve endings located in the diaphragm 18. The assembly 40 comprises a right loop 41 and a left loop 42, each loop comprising a plurality of electrodes 41a-h and 42a-h, each having individual connectors and leads that form leads 43, 44 coupled to the control unit 100. The loops 41, 42 are similar to electrode assemblies 41, 42 in that the electrodes are selectable by the control unit 100 to form electrode pairs, multiple electrode pairs, or multipolar electrode groups. FIG. 2 illustrates right phrenic nerve endings 15a and left phrenic nerve endings 16a as well as the right phrenic nerve anterior branch 15b, and left phrenic nerve anterior branch 16b, located on the diaphragm abdominal surface 18s. The loops 41, 42 are flexible and are placed on the abdominal surface 18s of the diaphragm 18 on the right diaphragm 18r and left diaphragm 18l, respectively adjacent the right phrenic nerve endings 15a and left phrenic nerve endings 16a respectively. The flexibility of the loops 41, 42 permits the ability to form the loops is the shape most ideally suite for a particular patient. The loops 41, 42 are attached to the diaphragm 18 with sutures, staples or other attachment devices 19. Other shapes may be used as well, e.g. a loop with a branch that extends to the region adjacent the anterior branches 15b, 16b of the phrenic nerve. The control unit 100 may be programmed to activate the electrodes in a sequence that is determined to elicit the desired response from the diaphragm 18 as described above with reference to electrodes 21a-d, 22a-d and FIG. 1.

Referring to FIG. 3, a breathing disorder treatment apparatus 60 according to the invention is illustrated. The apparatus 60 comprises right and left electrode assemblies 61, 62 each comprising a plurality of electrodes 61a-61d and 62a-62d respectively. The electrodes assemblies 61, 62 are illustrated attached to the right and left phrenic nerves 15, 16, respectively at a location in the neck 17. The electrode assembly may be a curved cuff electrode that can be placed around the nerve. Procedures for accessing and attaching such electrode assemblies are generally know, for example, as described in *Phrenic Nerve Stimulation For Diaphragm Pacing With a Spinal Cord Stimulator*, Sur. Neurol 2003:59: 128-32.

FIG. 4 illustrates the device 60 of to FIG. 3 with electrode assemblies 61, 62 alternatively positioned within the thorax 19 on the phrenic nerves 15, 16. The electrode assemblies 61, 62 are placed thoracoscopically on the phrenic nerve using a procedure similar to that described in *Thoracoscopic Placement of Phrenic Nerve Electrodes for Diaphragmatic Pacing in Children*; Journal of Pediatric Surgery, Vol. 37, No 7 (July), 2002: pp 974-978. The electrode assemblies 61, 62 are located between the third and fourth rib within the thorax 19. The stimulator 60 is used in a similar manner in this FIG. 4 as it is with reference to FIG. 3.

FIG. 5 illustrates a stimulator 70 in accordance with the invention. The stimulator comprises stimulating electrode assemblies 71, 72 implanted in the diaphragm in a manner similar to that described above with reference to electrode assemblies 71, 72 in FIG. 1. The electrode assemblies 71, 72 include electrodes 71a-d, 72a-d, configured to deliver stimulating pulses to the diaphragm and or phrenic nerve branches or junctions with the diaphragm to elicit a breathing response by causing the diaphragm to move. The stimulator 70 further comprises electrode sensor assemblies 75, 76 placed on the phrenic nerve at the throat in a surgical procedure similar to that described above with reference to FIG. 1 and electrode assemblies 71, 72. The sensor assemblies 75, 76 comprise a plurality of electrodes that are positioned and configured to sense electrical activity of the phrenic nerve to determine central respiratory effort. In response to sensed respiratory effort, the control unit 100 supplies EMG and/or nerve stimulation to the muscles of the diaphragm 18 and/or the phrenic nerve endings 15, 16 located in the diaphragm 18.

FIG. 6 illustrates an implantable control unit 100. The control unit 100 includes electronic circuitry capable of generating and/or delivering electrical stimulation pulses to the electrodes of electrode assemblies 21, 22, 41, 42, 61, 62, 71, 72 through leads 23, 24, 43, 44, 63, 64, 73, 74 respectively to cause a diaphragm respiratory response in the patient. For purposes of illustration, in FIG. 6, the control unit 100 is illustrated coupled to through leads 23, 24 to electrode assemblies 21, 22 respectively. Other leads 41, 42, 61, 62, 71, 72 as described herein may be connected to inputs 101, 102.

The control unit 100 comprises a processor 105 for controlling the operations of the control unit 100. The processor 105 and other electrical components of the control unit are coordinated by an internal clock 110 and a power source 111 such as, for example a battery source or an inductive coupling component configured to receive power from an inductively coupled external power source. The processor 105 is coupled to a telemetry circuit 106 that includes a telemetry coil 107, a receiver circuit 108 for receiving and processing a telemetry signal that is converted to a digital signal and communicated to the processor 105, and a transmitter circuit 109 for processing and delivering a signal from the processor 105 to the telemetry coil 107. The telemetry coil 107 is an RF coil or alternatively may be a magnetic coil. The telemetry circuit 106 is configured to receive externally transmitted signals, e.g., containing programming or other instructions or information, programmed stimulation rates and pulse widths, electrode configurations, and other device performance details. The telemetry circuit is also configured to transmit telemetry signals that may contain, e.g., modulated sensed and/or accumulated data such as sensed EMG activity, sensed nerve activity, sensed responses to stimulation, sensed position information, sensed movement information and episode counts or recordings.

The leads 23, 24 are coupled to inputs 101, 102 respectively, of the control unit 100, with each lead 23, 24 comprising a plurality of electrical conductors each corresponding to one of the electrodes or sensors (e.g., strain gauge) of the electrode assemblies 23, 24. Thus the inputs 101, 102 comprise a plurality of inputs, each input corresponding to one of the electrodes or sensors. The signals sensed by the electrode assemblies 21, 22 are input into the control unit 100 through the inputs 101, 102. Each of the inputs are coupled to a separate input of a signal processing circuit 116 (schematically illustrated in FIG. 6 as one input) where the signals are then amplified, filtered, and further processed, and where processed data is converted into a digital signal and input into the processor 105. Each signal from each input is separately processed in the signal processing circuit 116.

The EMG/Phrenic nerve sensing has a dual channel sensor. One corresponding to each lung/diaphragm side. However, sensing can be accomplished using a single channel as the brain sends signals to the right and left diaphragm simultaneously. Alternatively, the EMG or phrenic nerve collective may be sensed using a single channel. Either a dual channel or single channel setting may be used and programmed. The typical pulse width parameter will range from 0.5 ms to 10 ms in increments of 50 µs. The pulse amplitude is from about 0.1 v to 5 volts in increments of 100 µV. The refractory period is 1 to 10 seconds in increments of 1 second. As described in more detail with reference to FIGS. 10A-10B herein the system may adjust the pace, pulse, frequency and amplitude to induce or control rate of the various portions of a respiratory cycle, e.g. slope of inspiration, fast exhalation, exhalation and tidal volume. The system may also adjust the rate of the respiratory cycle.

The system EMG memory is programmable to pre-trigger and post trigger lengths of storage for sleep apnea episodes. The pre-trigger events are the waveform signals and other sensed information observed transitioning to an event. Post-trigger events are the waveforms and other sensed information observed after an event and/or after treatment of an event, to observe how the device operated. Post-trigger recordings can confirm if the episode was successfully treated. The pre-trigger and post-trigger time periods can be preprogrammed into the control unit 100.

The control unit 100 includes a position sensor 121 configured to sense a relative position of the patient, e.g. angular position, and provide a digital signal corresponding to the sensed position to the processor 105.

The control unit 100 also includes an accelerometer 122 configured to sense acceleration and movement of the patient and to provide a digital signal corresponding to the sensed movement to the processor 105. In addition, an accelerometer 122 is positioned within the control unit 100. The accelerometer 122 measures the activity levels of the patient and provides the signal to the processor 105 for use in further analysis. Using an accelerometer in the implanted device indicates the activity level of the patient in conjunction with breathing rate. The accelerometer senses activity threshold as at rest, low medium or high depending on the programmed threshold value for a specific patient. Using the activity (accelerometer) sensor value and respiratory information, the health of the respiratory system may be evaluated and monitored. For example, if a patient's respiratory rate increases with an increase in activity and decreases with a decrease in activity, within a normal range, the patient's system will be considered functioning normally. If the patient's respiratory rate is out of range or too high while the activity sensor indicates at rest or low, then the patient may be suffering from pulmonary edema. Using this monitor, the effect of drug titrations, e.g., diuretic dosages, on a patient with pulmonary edema can be monitored. If the pulmonary edema patient's respiration is brought more towards a normal range with a drug dose, then the drug treatment would be maintained. If the drug treatment did not effect breathing sufficiently then the drug dosage may be increased. Accordingly, the drug dosage may vary with detected breathing irregularities.

A position sensor 121 is also located within the control unit 100 and has an output coupled to the processor 105. The position sensor senses the relative angle of the patients' position. The position sensor is used to detect a patient's relative position, e.g., horizontal, supine, or standing. An available position sensor is the Spectrol 601-1045 smart position sensor, self-contained device that provides an analog output over a full range of 360 degrees without requiring external components.

The control unit 100 further includes a ROM memory 118 coupled to the processor 105 by way of a data bus. The ROM memory 118 provides program instructions to the control unit 100 that direct the operation of the stimulator 40. The control unit 100 further comprises a first RAM memory 119 coupled via a data bus to the processor 105. The first RAM memory 119 may be programmed to provide certain stimulation parameters such as pulse or burst morphology; frequency, pulse width, pulse amplitude, duration and a threshold or trigger to determine when to stimulate. A second RAM memory 120 (event memory) is provided to store sensed data sensed, e.g., by the electrodes 21$a$-$d$ 22$a$-$d$, 41$a$-$h$ 42$a$-$h$, 61$a$-$d$ 62$a$-$d$, 71$a$-$d$, 72$a$-$d$ (EMG or nerve activity), position sensor 121, diaphragm movement sensors or strain gauges 25, 26, or the accelerometer 122. These signals may be processed and used by the control unit 100 as programmed to determine if and when to stimulate or provide other feedback to the patient or clinician. Also stored in RAM memory 120 may be the sensed waveforms for a given interval, and a count of the number of events or episodes over a given time as counted by the processor 105. The system's memory will be programmable to store: number of sleep apnea episodes per night; pacing stimulation and length of time; the systemic auto-correction (i.e., how stimulus was adjusted, e.g., in amplitude frequency phase or waveform, to reach a desired or intrinsic level response); body resumption of breathing; the number of apnea episodes with specific durations and averages and trending information; hyperventilation episodes during supine position; number of hyperventilation episodes during sleep position; number of hyperventilation episodes during vertical position; and patient information including the medications and dosages and dates of changes. These signals and information may also be compiled in the memory and downloaded telemetrically to an external device 140 when prompted by the external device 140.

An example of the circuits of the signal processing circuit 116 corresponding to one of the EMG inputs for one of the electrodes or pairs of electrodes of the assemblies 21, 22 is illustrated schematically in FIG. 7A. An EMG signal is input into an amplifier 130 that amplifies the signal. The signal is then filtered to remove noise by filter 131. The amplified signal is rectified by a rectifier 132, is converted by an A/D converter 133 and then is integrated by integrator 134 to result in an integrated signal from which respiratory information can be ascertained. The signal output of the integrator 134 is then coupled to the processor 105 and provides a digital signal corresponding to the integrated waveform to the processor 105. The signal output of the integrator 134 is also coupled to a peak detector 135 that determines when the inspiration period of a respiratory cycle has ended and an expiration cycle has begun. The signal output of the integrator 134 is further coupled to a plurality of comparators 136, 137, 138, 139. The first comparator 136 determines when respiration (EMG signal or phrenic nerve signal) has been detected based on when an integrated signal waveform amplitude has been detected that is greater than a percentage value of the peak of an intrinsic respiratory cycle or another predetermined amount (comp 1), for example between 1-25% of the intrinsic signal. In this example, the comparator is set at a value that is 10% of the waveform of an intrinsic respiratory cycle. The second comparator 137 determines a value of the waveform amplitude (comp 2) when an integrated signal waveform amplitude has been detected that is at a predetermined percentage value of the peak of an intrinsic respiratory cycle or another predetermined amount, for example between 75%-100% of the intrinsic signal. In this example, the comparator is set at a value that is 90% of the waveform of an intrinsic respiratory cycle. From this value and the comp 1 value, the slope of the inspiration period (between 10% and 90% in this example) may be determined. This slope may provide valuable diagnostic information as it shows how quickly a patient inhales. After (or when) the peak detector detects the end of an inhalation period and the beginning of an exhalation period, the third comparator 138 determines an upper value for the waveform amplitude during active exhalation period, for example between 100% and 75% of the peak value detected by the peak detector 135. Then a lower value (comp 4) of the waveform during the exhalation period is determined by the fourth comparator 139, which compares the measured amplitude to a predetermined value, e.g. a percentage value of the peak amplitude. In this example the value is selected to be 10% of the peak value. In one embodiment this value is selected to roughly coincide with the end of a fast exhalation period.

From comp 3 and comp 4 values, the slope of the exhalation period (between 10% and 90% in this example) may be determined. This slope may provide valuable diagnostic information as it shows how quickly a patient exhales.

FIG. 7B illustrates two sequential integrated waveforms of exemplary integrated signals corresponding to two serial respiratory cycles, described in more detail herein with reference to FIGS. 9A-9D. The waveform 170 has a baseline 170b, inspiration cycle 171, a measured inspiration cycle 172, a point of 10% of peak inspiration 173 (comp 1), a point of 90% of peak of inspiration 174 (comp 2), a peak 175 where inspiration ends and exhalation begins, and exhalation cycle 176 a fast exhalation portion 177 of the exhalation cycle 176, a 90% of peak exhalation point 178 (comp 3), a 10% of peak exhalation point 179 (comp 4), an actual respiratory cycle 180 and a measured respiratory cycle 181. The second waveform 182 is similarly shaped. The 10% inspiration 183 of the second waveform 182 marks the end of the measured respiratory cycle 181, while the 10% point 173 of the waveform 170 marks the beginning of the measured respiratory cycle 181.

The system may adjust the pace, pulse, frequency and amplitude to induce slow and elongated inspiration period; and fast and short inspiration period. The system may match the intrinsic sleep or awake time tidal volume by adjusting the output energy while sensing the EMG or nerve amplitude. This may be done gradually by frequently sensing and incrementally adjusting. The system may deliver elongated inspiration period while shortening the expiration period to control and manipulate the $PO_2$ and $PCO_2$ levels in the blood to overcome and treat apnea. The system may deliver time and amplitude modulation output for control of inspiration and exhalation periods. To increase the inspiration period, the system may deliver fewer bursts at lower amplitudes and higher frequencies. To create a fast, short inspiration cycle, the system may deliver more of bursts at higher amplitudes. The system may deliver sequential low energy pacing output either from one or multiple electrodes to control and manage the pulmonary stretch receptor threshold levels to avoid or prevent the collapse of the upper airways. FIG. 10 illustrates a variety of exemplary stimulation bursts and resulting effective EMG that may be used to control the various phases of the respiratory cycle, including, e.g., slope of inspiration, fast exhalation, exhalation, tidal volume, peak value, and rate of respiration.

Referring to FIGS. 10A-10B, a first intrinsic EMG waveform 550 is illustrated in FIG. 10A. A subsequent EMG waveform 551 (FIG. 10A) is illustrated in response to a burst of pulses 561 (FIG. 10B) of symmetric amplitude, frequency and pulse width. A subsequent EMG waveform 552 is illustrated (FIG. 10A) in response to burst of pulses 562 (FIG. 10B). The resulting EMG waveform 552 (FIG. 10A) has a flatter inspiration slope and expiration slope and relatively lower peak amplitude. This particular effect may be desirable to control breathing and create a slower more gradual inspiration. The burst 562 (FIG. 10B) comprises a series of pulses increasing in amplitude and of a higher frequency than burst 561 (greater number of pulses). The subsequent EMG waveform 553 (FIG. 10A) has a relatively sharp inspiration slope. The corresponding burst 563 of pulses has fewer pulses (3) and higher amplitude pulses. The effect of this burst 563 is to increase inspiration rate. The subsequent EMG waveform 554 (FIG. 10A) has a relatively slow inspiration cycle as a result of a burst 564 (FIG. 10B) with both increasing amplitudes and longer pulse widths (and a greater pulse duration). These are a few examples of a multitude of possible variations of burst pulses that can be modified to control the inspiration, expiration, tidal volume (area under waveform curve) and other parameters of the respiratory cycle by modifying frequency, amplitude, pulse width of the pulses within the burst and the duration of the burst to get a desired effect. These bursts can be modified and programmed into a stimulator and may vary from patient to patient.

In FIG. 8 a circuit for an external device 140 is illustrated. The external device 140 comprises a processor 145 for controlling the operations of the external device. The processor 145 and other electrical components of the external device 140 are coordinated by an internal clock 150 and a power source 151. The processor 145 is coupled to a telemetry circuit 146 that includes a telemetry coil 147, a receiver circuit 148 for receiving and processing a telemetry signal that is converted to a digital signal and communicated to the processor 145, and a transmitter circuit 149 for processing and delivering a signal from the processor 145 to the telemetry coil 146. The telemetry coil 147 is an RF coil or alternatively may be a magnetic coil depending on what type of coil the telemetry coil 107 of the implanted control unit 100 is. The telemetry circuit 146 is configured to transmit signals to the implanted control unit 100 containing, e.g., programming or other instructions or information, programmed stimulation rates and pulse widths, electrode configurations, and other device performance details. The telemetry circuit 146 is also configured to receive telemetry signals from the control unit 100 that may contain, e.g., sensed and/or accumulated data such as sensed EMG activity, sensed nerve activity, sensed responses to stimulation, sensed position information, or sensed movement information. Other information such as frequency and time of apnea, number of apnea events detected in a time interval or during a sleep cycle, parameter relating to pulmonary edema such as frequency of hyperventilation including time and patient position. This information may be stored in RAM event memory 158 or may be uploaded and through an external port 153 to a computer, or processor, either directly or through a phone line or other communication device that may be coupled to the processor 145 through the external port 153. The external device 140 also includes ROM memory 157 for storing and providing operating instructions to the external device 140 and processor 145. The external device also includes RAM event memory 158 for storing uploaded event information such as sensed information and data from the control unit, and RAM program memory 159 for system operations and future upgrades. The external device also includes a buffer 154 coupled to or that can be coupled through a port to a user-operated device 155 such as a keypad input or other operation devices. Finally, the external device 140 includes a display device 156 (or a port where such device can be connected), e.g., for display visual, audible or tactile information, alarms or pages.

The external device 140 may take or operate in, one of several forms, e.g. for patient use, compliance or monitoring; and for health care provider use, monitoring, diagnostic or treatment modification purposes. The information may be downloaded and analyzed by a patient home unit device such as a wearable unit like a pager, wristwatch or palm sized computer. The downloaded information may present lifestyle modification, or compliance feedback. It may also alert the patient when the health care provider should be contacted, for example if there is malfunctioning of the device or worsening of the patient's condition. The system may prompt the patients with voice, music or other audible alarms regarding compliance with medication, diet and exercise. Medication compliance is a major issue with heart failure patients due to the difficulties created for the patients by some medications. The patient hand held also provides daily update regarding the status of the device and as well as whether patients need to see the physician and/or consuming more or less of a medication according to the programmed parameters by the physician inside the implantable device. The device may also manage a patient's diuretic level in relationship to breathing frequency and character. The device may monitor the response of the treatment from measured parameters provided by the control unit 100 in response to diuretic usage that e.g., may be input by the patient. This system may also warn the patient to check into a hospital based on physician command (programming). The system could also direct the patient to rest in different positions to alleviate the present problem until help arrives.

Another device that interfaces with the patient's home unit may also be used to provide information to the clinicians. Such device may communicate, for example via an internet, phone or other communication device. It may download information from the patient and/or upload information form the physician. It may provide physicians with information identifying when intervention may be necessary or to further diagnose a patient's condition.

The external device may be equipped with a palm pilot type device that connects to the phone line for downloading the patient specific information regarding patient's pulmonary status as well as of conditions including apnea, hypoventilation and hyperventilation, and whether the parameters are programmed correctly. This device may allow for remote follow-up, continuous monitoring of the patient's hemodynamic status, effectiveness of the drug regime and in particular the management of diuretics where the apnea is influenced by pulmonary edema. The information may be viewed by the clinician using a web browser anywhere in the world of the handheld can send a fax or notice to the physician's office once the parameters of interest are outside the programmed range. The physician may then request an office visit. The system also can send a summarized report on weekly, biweekly, or monthly as routine update based on the decision of the physician programmed in the handheld device. Medication adjustment/drug titration may be accomplished remotely. Hand-held communication protocol/technology may be magnetic or RF.

FIGS. 9A-9D illustrate the operation of a stimulator in accordance with the invention. The EMG monitoring is turned on or started 200. (Alternatively, or additionally, the phrenic nerve activity may be monitored in the sequences described in FIGS. 9A-9D). As illustrated in FIG. 9A-9B, the system is turned on and begins sensing respiratory effort. It determines the intrinsic rates of breathing cycles including respiratory period, inhalation period and exhalation period, and stores the values in event memory (step 200). This may be done, e.g., by sensing when a patient is in a reclining position for a predetermined period of time while their breathing normalizes to that near the breathing rate when sleeping. A threshold level is then calculated from the intrinsic rate at some level below the peak of the intrinsic respiratory effort level.

The presence of an EMG is detected 200 by detecting when the amplitude of the integrated waveform 170 reaches a predetermined level, e.g., at a percentage of the total amplitude, of the intrinsic waveform of the breathing rate when sleeping.

If there is no EMG detected 201 then the stimulator determines whether sleep apnea is present or not 300 by determining a lack of EMG or phrenic nerve activity in a given period of time, e.g., 5-10 seconds, or by an attenuated EMG, e.g., not reaching comp 1 or, e.g., not reaching comp 2 in the case of partial apnea. If sleep apnea is present, then the stimulator goes to the apnea treatment module 301 or to a program where the apnea is treated (See FIG. 9B). If sleep apnea is not detected, then the stimulator determines if hypoventilation is present 400 by determining that the EMG is present at an intrinsic amplitude or percentage thereof, but the rate is lower than the intrinsic rate. If hypoventilation is present then the stimulator goes to the hypoventilation treatment module 401 or to a program where hypoventilation is treated. (See FIG. 9C.) If an EMG, apnea, and hypoventilation are not detected, then presumably the patient is not breathing or there is a malfunctioning of the stimulator. If this is the case, the system may be programmed to do an emergency check of the components and then communicate to the patient or health care provider that the stimulator is malfunctioning and/or the patient is not breathing 250. This communication may be accomplished a number of ways via a variety of ongoing or periodic communication processes. The system may continue to listen for an EMG 201 after the system does and emergency check (step 250). After a given time or number of iterations of reaching step 250, the stimulator may sound an alarm.

If an EMG is detected at step 201, then the stimulator starts a respiratory timer 202 and the time and amplitude values are stored. The respiratory timer will determine the amount of time in one given breathing cycle between the detected beginning of inspiration, exhalation and the detected beginning of the inspiration of the next cycle. The inspiration timer will also be started 203. The inspiration timer will time the duration of inspiration when detected, as described with respect to step 201, until the peak of the inspiration or the beginning of expiration.

The slope of the inspiration cycle is determined 204 by determining the amplitude and time of that amplitude at a further point in time in the inspiration cycle (comp 2) from this information and the time and amplitude at the detection of the EMG (201).

A peak detector monitors the integrated waveform and determines when it has peaked 205, marking the end of inspiration and the beginning of expiration. When the peak is detected the time or duration of the inspiration cycle is stored along with the amplitude 206. The inspiration timer is then turned off 207 and the exhalation timer is started 208. In step 209 the values comp 3 and comp 4 are determined as a predetermined percentage to the peak value. In step 210, a comparator will then compare the amplitude of the signal during exhalation to a predetermined value or percentage of the total amplitude as measured at the peak until that value is reached. This predetermined value is referred to herein as comp 3. The time is stored. In step 211, a comparator will then compare the amplitude of the signal during exhalation to a predetermined lower end value or percentage of the total amplitude as measured at the peak until that value is reached. This predetermined value is referred to herein as comp 4. The stimulator then determines the slope of the exhalation cycle based on time and amplitude values of comp 3 and comp 4. The value for comp 4 may be selected to approximately mark the end of the fast exhalation period of the exhalation cycle, which is the initial period where the exhalation is sharper. At this point, the exhalation timer is stopped and the amplitude value and time is stored 212. In step 213, the stimulator may then determine the inhalation period, the exhalation period and the slope or curve characteristics of the breathing cycle during this time the slope of the waveform during either exhalation and/or inspiration may be recorded and analyzed to identify breathing irregularities. The inhalation period and exhalation period may be respectively based on the time values between the beginning of inhalation (comp 1) and the peak, and the peak (for inspiration) and the beginning of the peak and the end of the fast exhalation period. Also, the inspiration and expiration periods may also respectively include a calculation or approximation of the time between the actual beginning of inspiration to the detected beginning of inspiration and a calculation of the time between the end of the fast exhalation (comp 4) and the end of the exhalation period. The slopes of each of the inspiration periods and expiration periods may be calculated as well as the determination of other waveform characteristics that may provide useful diagnostic information. After the end of the fast exhalation period has been determined the stimulator then determines the total respirator period. After a first inhalation and exhalation cycle of a first breath, the stimulator awaits to detect a second cycle. The stimulator waits to detect the presence of a comp 1 value of an EMG 215. If the EMG is present then the time is stored, the respiratory timer is stopped, and the respiratory period is stored 216. The respiratory period may be a measured time from the detection of an EMG of a first waveform to the detection of an EMG of a second waveform. Alternatively, the respiratory period may be determined by adding the initial undetected period of the first waveform and subtracting the initial undetected period of the second waveform. The stimulator then determines if there is hyperventilation 217 by determining if the rate is a certain value or amount above the intrinsic rate for the particular awake, sleep or other state of the patient. If hyperventilation is detected, then the stimulator goes to the hyperventilation module 501 where hyperventilation is treated. If no hyperventilation is detected, the stimulator returns to its original monitoring step 201 where it awaits the next EMG detection and repeats the cycle.

FIG. 9B illustrates the sleep apnea module 301. When sleep apnea is detected 300, a determination is made as to whether apnea is complete apnea 302. Complete apnea would be determined by a complete lack in effective or detected EMG (or alternatively, phrenic nerve activity). If the apnea is not sleep apnea then a determination is made as to whether the apnea is partial apnea 320 where the EMG signal is attenuated a predetermined amount. If the apnea is obstructive apnea, an out of phase EMG may be detected as well.

If complete sleep apnea is detected 302, then the pacing output parameters stored in RAM 120 are loaded 303, e.g., into a register. The pacing output is then delivered 304. After delivering the pacing output to the phrenic nerve and/or diaphragm muscle, the EMG is observed 305, if the EMG is not approximately at the intrinsic sleep level, then the parameters are adjusted to bring the EMG more within the appropriate range 306 and elicit a response closer to intrinsic breathing. For example, if the frequency or amplitude is too low, then the frequency or amplitude of the pacing is adjusted upwards. If the frequency or amplitude is too high, then the frequency or amplitude of the pacing is adjusted downward. If the EMG is approximately at the intrinsic sleep level 305, then the monitoring period is increased by one second 307 (e.g., the monitoring period may start at about 10 seconds with a maximum at about 15 seconds). The EMG is then monitored again to see if apnea is present 308. If it is then the pacing output is continued 304. If it is then, if the monitoring period is not at a defined maximum 309 then the monitoring period is increased one second and the EMG is observed again 308 and as long as the EMG is present 308, the stimulator will keep increasing the monitoring period by one second 307 until the maximum monitoring period is reached 309. When the monitoring period does reach a maximum level, the apnea is confirmed as being treated 310 by observing the EMG for a given period of time, e.g. for 3 consecutive EMG's. The parameters of stimulation and information regarding the episode are stored 311 in event RAM 119, and the system returns to EMG monitoring (step 200 of FIG. 9A).

If complete sleep apnea is not detected 302 then the stimulator determines if partial apnea is present 320. If partial apnea is not present, the system returns to the emergency check 250 to see if the system is malfunctioning. If partial apnea is present, then the existing EMG parameters are determined 321 and the pacing parameters are adjusted based on the existing EMG 322 and are loaded 323 and are delivered 324. The existing EMG parameters may be determined a number of ways. The system may attempt to match the desired EMG with the pacing output by adding on to the existing EMG. One method may involve calculating the tidal volume based on the peak value of the existing EMG voltage output, pulse width, thus area under the respiration curve; calculating the pacing energy (amplitude and frequency) required to achieve the tidal volume (of an intrinsic sleep EMG); and increasing the EMG or pacing an increased calculated amount to achieve the desired tidal volume.

If after delivering the pacing output 324, the EMG is not at the intrinsic sleep level 325, then the parameters are adjusted to elicit the intrinsic response 331 and the parameters are loaded 3232 and delivered 324 again. If the EMG is at the intrinsic sleep level 325 then the monitoring period is increased by one second 326, and EMG observed again to determine if the partial apnea has been treated 327. If the apnea has not been treated, then the stimulator returns to delivering the pacing output 324. If apnea has been treated and the monitoring period is not at the maximum 328 then the monitoring time is increased by one second 326, and partial apnea is detected 327, etc. until the monitoring period has reached its maximum time 328 throughout which apnea is determined to have been successfully treated. After the maximum period is reached apnea treatment is confirmed 329 by observing the EMG a predetermined period of time afterwards, e.g., for three consecutive EMG's. The parameters and information regarding the episode are then stored 330. The system then returns to detecting the EMG (step 200 of FIG. 9A).

FIG. 9C illustrates the hypoventilation module 401. After hypoventilation is detected 400 by comparing the breathing rate to a programmed low threshold breathing rate for a particular condition or state (e.g., waking, resting or sleeping), a pacing output designed to elicit the intrinsic rate is loaded and is delivered to the phrenic nerve and/or diaphragm 403. The EMG is then sensed 404 and the EMG is compared to the intrinsic EMG amplitude and waveform 405. The output of the amplitude, rate and pulse width are adjusted to match intrinsic EMG morphology 406. The monitoring period is then increased by one second 407. If the natural breathing rate has been restored for the maximum monitoring period, the stimulator returns to the step of detecting presence of EMG (step 200, FIG. 9A). If it has not, then the EMG is sensed again 404, compared to the intrinsic rate 405, adjusted if necessary 406, and the timer incremented again 407 until the natural breathing has been restored 408.

FIG. 9D illustrates the hyperventilation module 501. If hyperventilation is present 500, then the level of hyperventilation is classified as Class I (low), Class II (medium) or Class III (high) based on the rate an frequency of hyperventilation. These particular rates and classifications may vary from patient to patient and may be programmed in by the health care provider. The time date, respiratory rate, frequency of hyperventilation and activity sensor are sensed and stored in event RAM 119. If class I is determined 504, the patient is informed via the handheld or home monitoring device 505 and the patient is notified to further comply with diuretic medications 506. If class II is detected 507, then the patient is informed and additional medication is recommended based on a prescription programmed into the hand held device 508. The device then requests feedback by way of the hand held device, regarding compliance 509. The health care provider is notified of the status by way of the remote system, telephone connection or otherwise, and the sensed information concerning the patient's status is uploaded 510. If class III is detected 511, then the patient is requested to visit the physician immediately and also to consume addition medication according to the physician's recommendation 512. The health care provider is notified via the remote system 512. The system then returns to detecting and EMG (step 200, FIG. 9A).

While the invention has been described with reference to particular embodiments, it will be understood to one skilled in the art that variations and modifications may be made in form and detail without departing from the spirit and scope of the invention.

What is claimed is:

1. A device for managing respiration patient having a sleep breathing disorder comprising:
    at least one electrode in electrical communication with a diaphragm or phrenic nerve tissue of a patient's body configured to sense respiration;
    a control unit in electrical communication with the at least on electrode and whereby the control unit receives sensed respiration activity,
    wherein the control unit is programmed to identify the intrinsic breathing cycle of the patient and create an intrinsic baseline profile thereof:
    wherein the control unit is further programmed to generate an electrical stimulation signal in response to the sensed respiration and deliver the electrical stimulation signal through the at least one electrode to the diaphragm or phrenic nerve tissue, wherein said control unit is programmed to deliver an electrical stimulation signal comprising a burst or series of pulses during an existing inspiration to adjust the breathing cycle of said patient,
    wherein the control unit is further programmed to monitor the adjusted breathing cycle of the patient, compare it against the patient's baseline intrinsic level and when the breathing is not at a desired level, to then adjust one or more parameters of the electrical stimulation signal and provide stimulation with each breath to incrementally adjust until the breathing cycle is further adjusted to reach the desired level, and
    wherein the electrical stimulation signal is configured to elicit a diaphragm response by stimulating to increase an existing inspiration duration which supplements a breath.

2. A device for managing respiration of a patient comprising:
    at least one electrode in electrical communication with a diaphragm or phrenic nerve tissue of a patient's body, wherein at least one of said electrodes is configured to sense respiration;
    a control unit in electrical communication with the at least one electrode whereby the control unit receives respiration activity sensed by at the least one electrode,
    wherein the control unit is programmed to generate an electrical stimulation signal in response to the sensed respiration and deliver the electrical stimulation signal through the at least one electrode to the diaphragm or phrenic nerve tissue, wherein said control unit is programmed to deliver the electrical stimulation signal as a burst or series of pulses during an existing inspiration to adjust the breathing cycle of said patient,
    wherein the control unit is further programmed to monitor the adjusted breathing cycle of the patient and compare against the patient's intrinsic level and to then adjust one or more parameters of the electrical stimulation signal to incrementally adjust with each breath until the breathing cycle is further adjusted to reach a desired level, and
    wherein the electrical stimulation signal is configured to elicit a diaphragm response by stimulating to supplement an existing inspiration volume of a breath.

3. The device of claim 1 or 2 wherein the control unit is further programmed to elicit an inspiration rate different from an intrinsic inspiration rate.

4. The device of claim 1 wherein the control unit is programmed to deliver a stimulation signal to the tissue through the at least one electrode to elicit a slow elongated inspiration.

5. The device of claim 1 wherein the control unit is programmed to deliver a stimulation signal to the tissue through the at least one electrode to elicit a fast, short inspiration.

6. The device of claim 1 or 2 wherein the control unit is further programmed to deliver low level sequential stimulations.

7. The device of claim 1 or 2 wherein the control unit is configured to deliver a stimulation signal that is directed to manipulating blood gases to thereby treat disordered breathing.

8. The device of claim 1 or 2 wherein said control unit is further programmed so that when the breathing has reached the desired level, the stimulation signal is no longer delivered.

\* \* \* \* \*

UNITED STATES PATENT AND TRADEMARK OFFICE
CERTIFICATE OF CORRECTION

Page 1 of 1

| | |
|---|---|
| PATENT NO. | : 8,467,876 B2 |
| APPLICATION NO. | : 10/686891 |
| DATED | : June 18, 2013 |
| INVENTOR(S) | : Tehrani |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1086 days.

Signed and Sealed this
Thirtieth Day of December, 2014

Michelle K. Lee
*Deputy Director of the United States Patent and Trademark Office*